United States Patent
Donavon

(10) Patent No.: US 10,922,995 B2
(45) Date of Patent: Feb. 16, 2021

(54) SYSTEMS AND METHODS FOR PROVIDING ANIMAL HEALTH, NUTRITION, AND/OR WELLNESS RECOMMENDATIONS

(71) Applicant: NESTEC SA, Vevey (CH)

(72) Inventor: Mark A. Donavon, Troy, IL (US)

(73) Assignee: SOCIÉTÉ DES PRODUITS NESTLÉ S.A., Vevey (CH)

( * ) Notice: Subject to any disclaimer, the term of this patent is extended or adjusted under 35 U.S.C. 154(b) by 376 days.

(21) Appl. No.: 14/793,304

(22) Filed: Jul. 7, 2015

(65) Prior Publication Data
US 2016/0012748 A1    Jan. 14, 2016

Related U.S. Application Data

(60) Provisional application No. 62/021,763, filed on Jul. 8, 2014.

(51) Int. Cl.
G09B 19/00 (2006.01)
G06F 19/00 (2018.01)
G09B 5/02 (2006.01)

(52) U.S. Cl.
CPC ......... G09B 19/00 (2013.01); G06F 19/3475 (2013.01); G09B 5/02 (2013.01); G09B 19/0092 (2013.01)

(58) Field of Classification Search
CPC ............................ G09B 19/00; G09B 19/0092
See application file for complete search history.

(56) References Cited

U.S. PATENT DOCUMENTS

| | | | |
|---|---|---|---|
| 6,234,111 B1* | 5/2001 | Ulman | A01K 1/031 119/51.02 |
| 2002/0021219 A1* | 2/2002 | Edwards | A01K 15/021 340/573.1 |
| 2005/0284381 A1* | 12/2005 | Bell | A01K 5/02 119/51.02 |
| 2006/0201433 A1* | 9/2006 | Kates | A01K 15/02 119/51.02 |
| 2008/0059264 A1 | 3/2008 | Stroman et al. | |
| 2010/0263596 A1* | 10/2010 | Schumann | A01K 5/0114 119/51.02 |
| 2012/0083669 A1 | 4/2012 | Abujbara | |
| 2012/0299731 A1* | 11/2012 | Triener | G01G 17/08 340/573.1 |

(Continued)

FOREIGN PATENT DOCUMENTS

| | | |
|---|---|---|
| JP | 2012518998 A | 8/2012 |
| WO | 2004027674 A1 | 4/2004 |

(Continued)

OTHER PUBLICATIONS

Fit bark. <https://www.kickstarter.com/projects/fitbark/fitbark-a-fitbit-for-dogs> <Jun. 25, 2013>.*

(Continued)

Primary Examiner — Robert J Utama

(57) ABSTRACT

The present disclosure is directed to systems and methods for preparing nutrition, health, and/or wellness recommendations for an animal. The systems and methods involve collecting data from the animal, analyzing the data, and providing the nutrition, health, and/or wellness recommendation based upon the analyzed data.

10 Claims, 27 Drawing Sheets

(56) References Cited

U.S. PATENT DOCUMENTS

| | | | | |
|---|---|---|---|---|
| 2013/0192526 | A1* | 8/2013 | Mainini | A01K 15/021 |
| | | | | 119/51.02 |
| 2013/0338453 | A1* | 12/2013 | Duke | A61B 5/7282 |
| | | | | 600/309 |
| 2014/0116341 | A1* | 5/2014 | Kopic | A01K 29/00 |
| | | | | 119/14.02 |
| 2014/0275852 | A1* | 9/2014 | Hong | A61B 5/02427 |
| | | | | 600/301 |
| 2014/0278220 | A1* | 9/2014 | Yuen | G01B 21/16 |
| | | | | 702/150 |
| 2015/0066520 | A1* | 3/2015 | Leon | G06F 19/3456 |
| | | | | 705/2 |
| 2015/0181840 | A1* | 7/2015 | Tupin, Jr. | A01K 27/009 |
| | | | | 600/483 |
| 2016/0000036 | A1* | 1/2016 | Cornwell, Jr. | A01K 5/0291 |
| | | | | 119/51.11 |
| 2016/0012748 | A1* | 1/2016 | Donavon | G09B 5/02 |
| | | | | 434/225 |
| 2016/0015004 | A1* | 1/2016 | Bonge, Jr. | A01K 27/009 |
| | | | | 119/718 |
| 2016/0015005 | A1* | 1/2016 | Brown, Jr. | A01K 29/005 |
| | | | | 340/573.3 |
| 2016/0029592 | A1* | 2/2016 | Springer | A01K 5/0225 |
| | | | | 119/51.11 |
| 2016/0192619 | A1* | 7/2016 | Gibbs | A01K 5/00 |
| | | | | 119/61.57 |
| 2016/0361021 | A1* | 12/2016 | Salehizadeh | A61B 5/0245 |
| 2017/0006838 | A1* | 1/2017 | Brayer | A01J 5/007 |

FOREIGN PATENT DOCUMENTS

| | | |
|---|---|---|
| WO | 2010033197 A1 | 3/2010 |
| WO | 2014050118 | 4/2014 |

OTHER PUBLICATIONS

Katherine. Tractive Motion. <http://www.lifewithdogs.tv/2014/12/tractive-motion-fitness-tracker-for-your-pet/> <Dec. 1, 2014>.*

Marselli et al. "Application of Kalman filtering to noise reduction on microsensor signals" Proceedings of the Colloque Interdisciplinaier en Insturmentation, C2L, 443-450, 1998 (Year: 1998).*

International Search Report and Written Opinion; PCT/IB2015/055145; dated Dec. 3, 2015.

Dunduo, "Clinical Diagnosis and Treatment as well as Malpractices in Veterinary Medicine", China Agricultural Press, Part I, Chapter III, 2006, pp. 43-47.

Office Action Received for Application No. CN201580036728.2, dated Aug. 5, 2020, 18 pages(9 pages of English Translation and 9 pages of Official Copy).

* cited by examiner

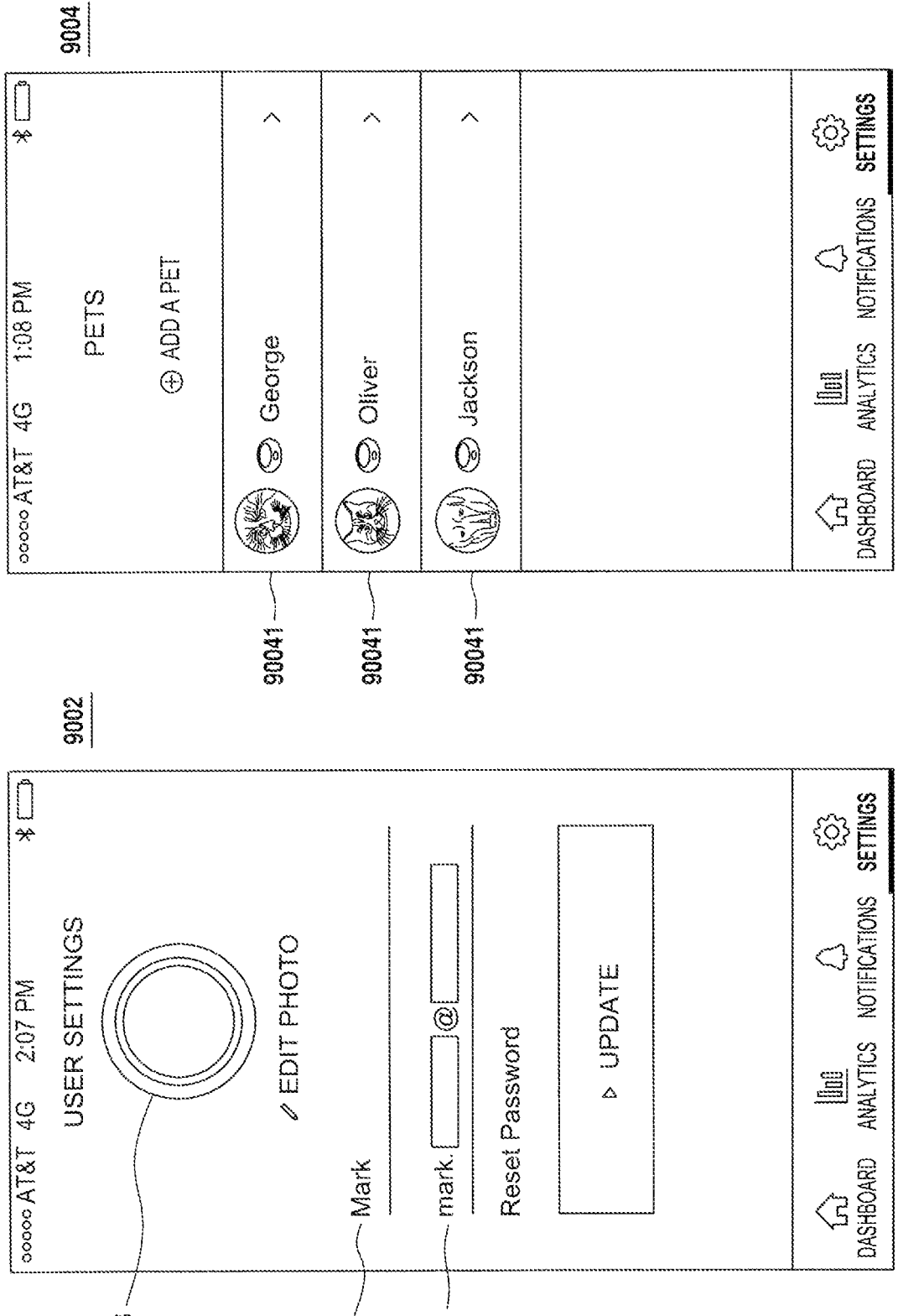

FIG. 9E ooooo AT&T 4G 1:10 PM

< CANCEL

BODY TYPE

What picture best resembles Spot?

UNDERWEIGHT  IDEAL  OVERWEIGHT

Ideal
Ribs palpable without excess fat covering. Waist observed behind ribs when viewed from above. Abdomen tucked up when viewed from side.

▷ NEXT

FIG. 9F ooooo AT&T 4G 1:10 PM

GREAT WORK!

has been successfully added!

▷ FINISH

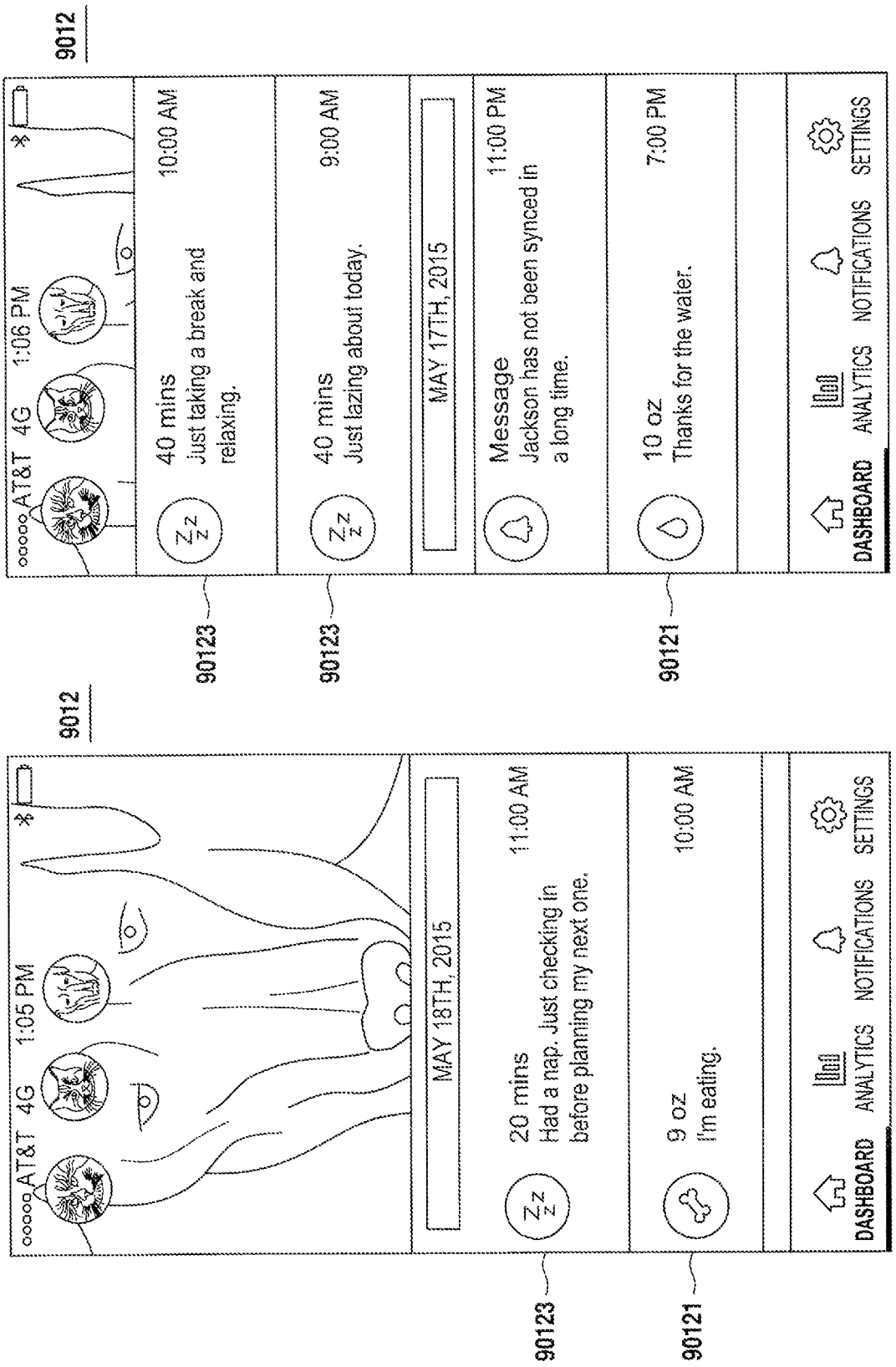

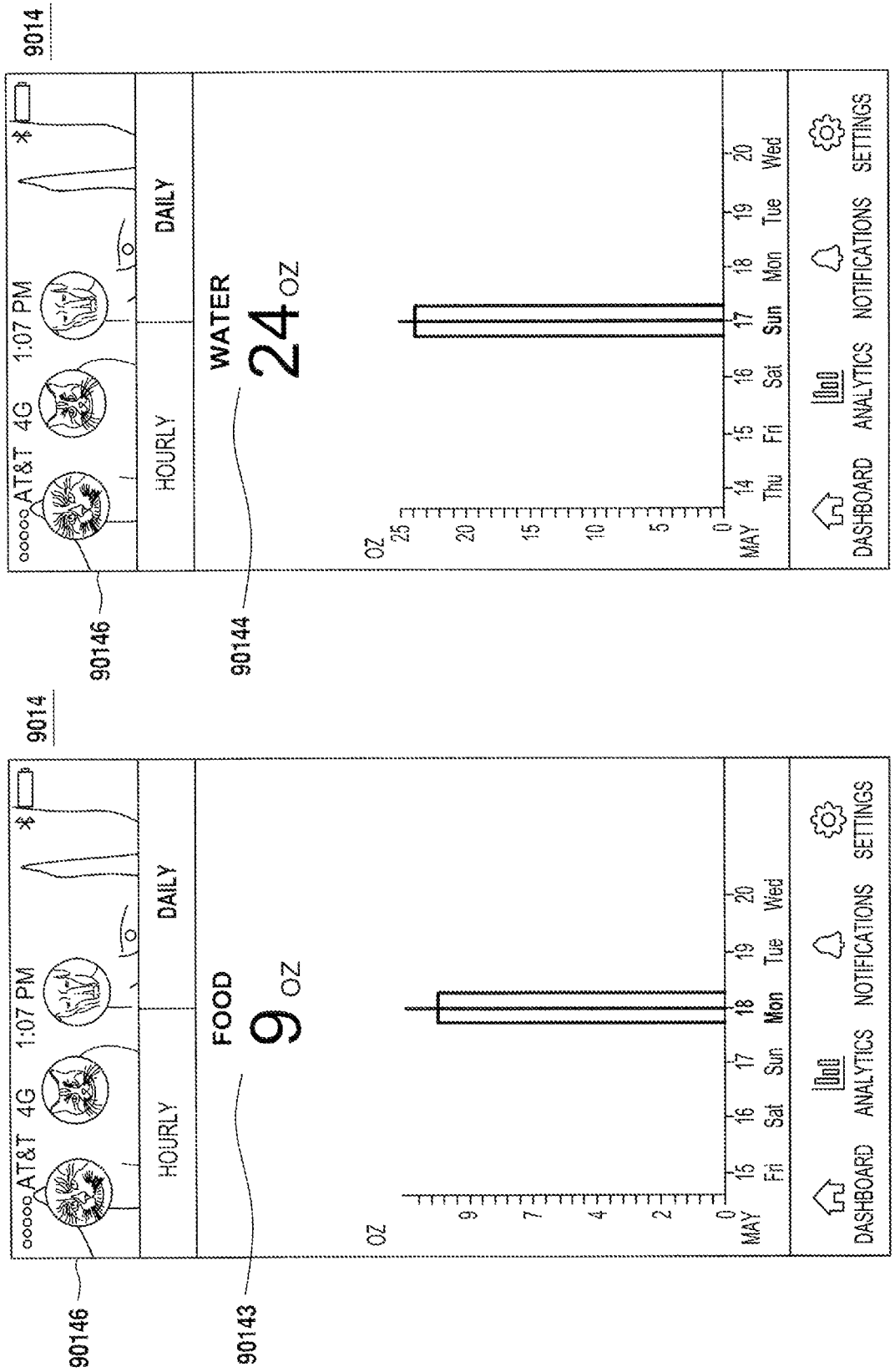

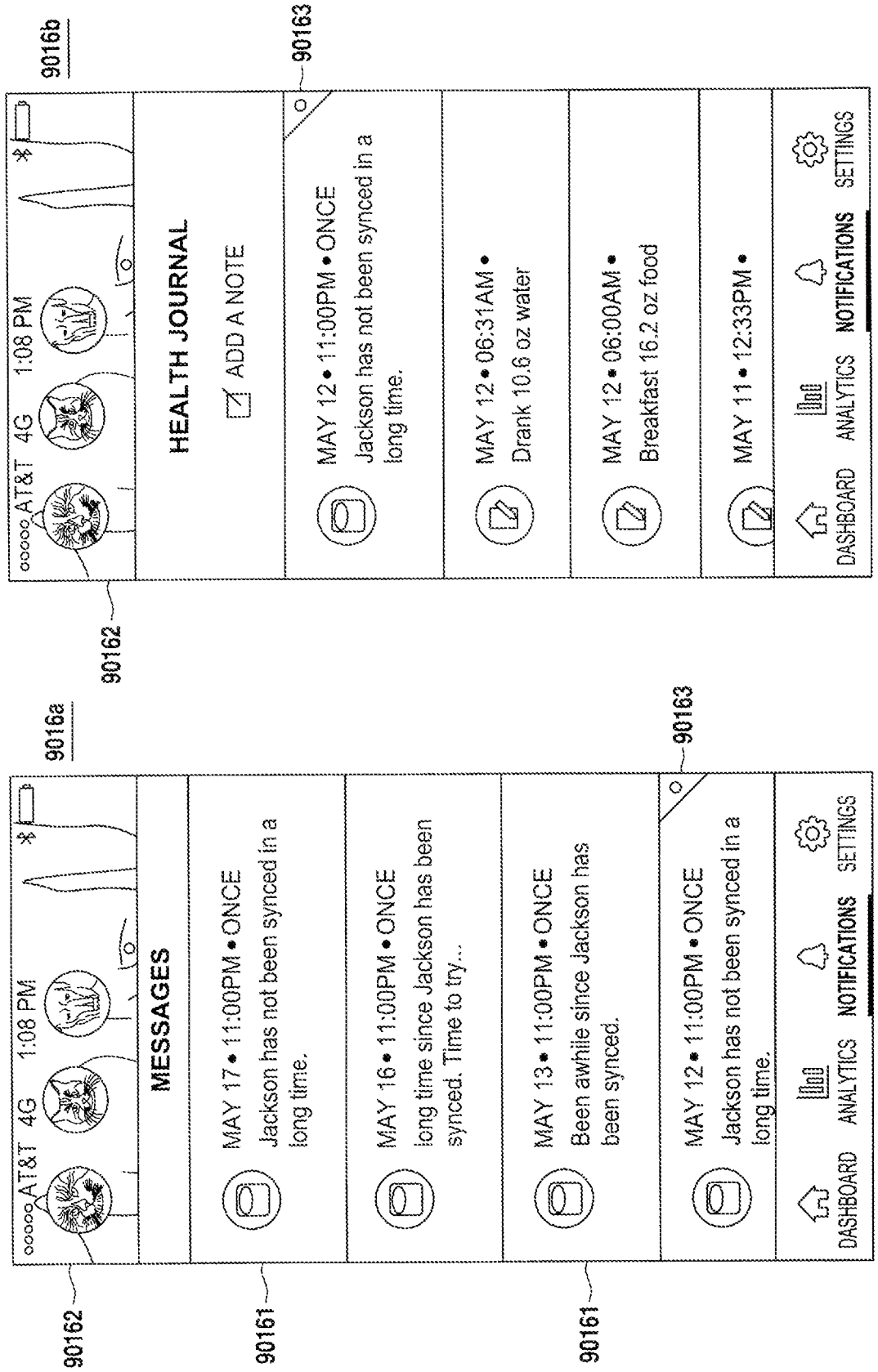

| Date | Weight | 3 day rolling avg. |
|---|---|---|
| 23 | 79.6 | |
| 24 | 80.7 | |
| 25 | 80.7 | 80.3 |
| 26 | 80.2 | 80.5 |
| 27 | 80.5 | 80.5 |
| 28 | 80.5 | 80.4 |
| 29 | 80.5 | 80.5 |
| 30 | 80.5 | 80.4 |
| 31 | 80.2 | 80.3 |
| 1 | 79.8 | 80.2 |
| 2 | 79.8 | 79.9 |
| 3 | 79.8 | 79.8 |
| 4 | 79.1 | 79.6 |
| 5 | 78.7 | 79.2 |
| 6 | 78.9 | 78.9 |
| 7 | 78.9 | 78.8 |
| 8 | 78.9 | 78.9 |
| 9 | 79.4 | 79.1 |
| 10 | 79.6 | 79.3 |
| 11 | 79.6 | 79.5 |
| 12 | 79.6 | 79.6 |
| 13 | 79.6 | 79.6 |
| 114 | 79.8 | 79.7 |
| 15 | 79.6 | 79.7 |
| 16 | 79.4 | 79.6 |
| 17 | 78.9 | 79.3 |
| 18 | 78.7 | 79.0 |
| 19 | 78.7 | 78.8 |

FIG. 18

SYSTEMS AND METHODS FOR PROVIDING ANIMAL HEALTH, NUTRITION, AND/OR WELLNESS RECOMMENDATIONS

CROSS-REFERENCE TO RELATED APPLICATIONS

This application claims priority to U.S. Provisional Patent Application No. 62/021,763, the contents of which are incorporated herein by reference in their entireties.

FIELD OF THE DISCLOSURE

The present disclosure generally relates to systems and methods for the provision of recommendations on improved nutrition, health, and/or wellness protocols using animal health, behavior, and/or environmental information.

BACKGROUND

Various approaches for animal health and behavior monitoring are known in the art. However, most approaches do not provide adequate interpretation of the data derived from such monitored data, nor is the interpretation communicated to the appropriate individuals in the form of insights about, and recommendations for, the animal.

SUMMARY OF THE DISCLOSURE

Among the various aspects of the present disclosure is the provision of methods of preparing a nutrition, health, and/or wellness recommendation for an animal. The recommendation (which may be, for example, in the form of a diet, exercise, medication/supplement, treatment protocol, and/or changes in animal owner and/or animal behavior), is prepared based upon data collected from the animal.

Briefly, therefore, the present disclosure is directed to a method of preparing a nutrition, health, and/or wellness recommendation for an animal. The method comprises collecting the data from the animal, analyzing the data, and providing the nutrition, health, and/or wellness recommendation based upon the analyzed data. Preferably, the collected data is one or more of a health, diet, behavior, or environmental parameter of the animal.

The present disclosure is also directed to systems and methods (including computer-implemented systems and methods) of preparing a nutrition, health, and/or wellness recommendation for an animal as substantially described herein.

Other objects and features will be in part apparent and in part pointed out hereafter.

BRIEF DESCRIPTION OF THE DRAWINGS

These and other features, aspects and advantages of the disclosure will become more fully apparent from the following detailed description, appended claims, and accompanying drawings, wherein the drawings illustrate features in accordance with exemplary aspects of the disclosure, and wherein:

FIG. 7 illustrates an exemplary user profile display of the mobile module.

FIG. 8 illustrates an exemplary animal profile display of the mobile module.

Figures 9C, 9D:
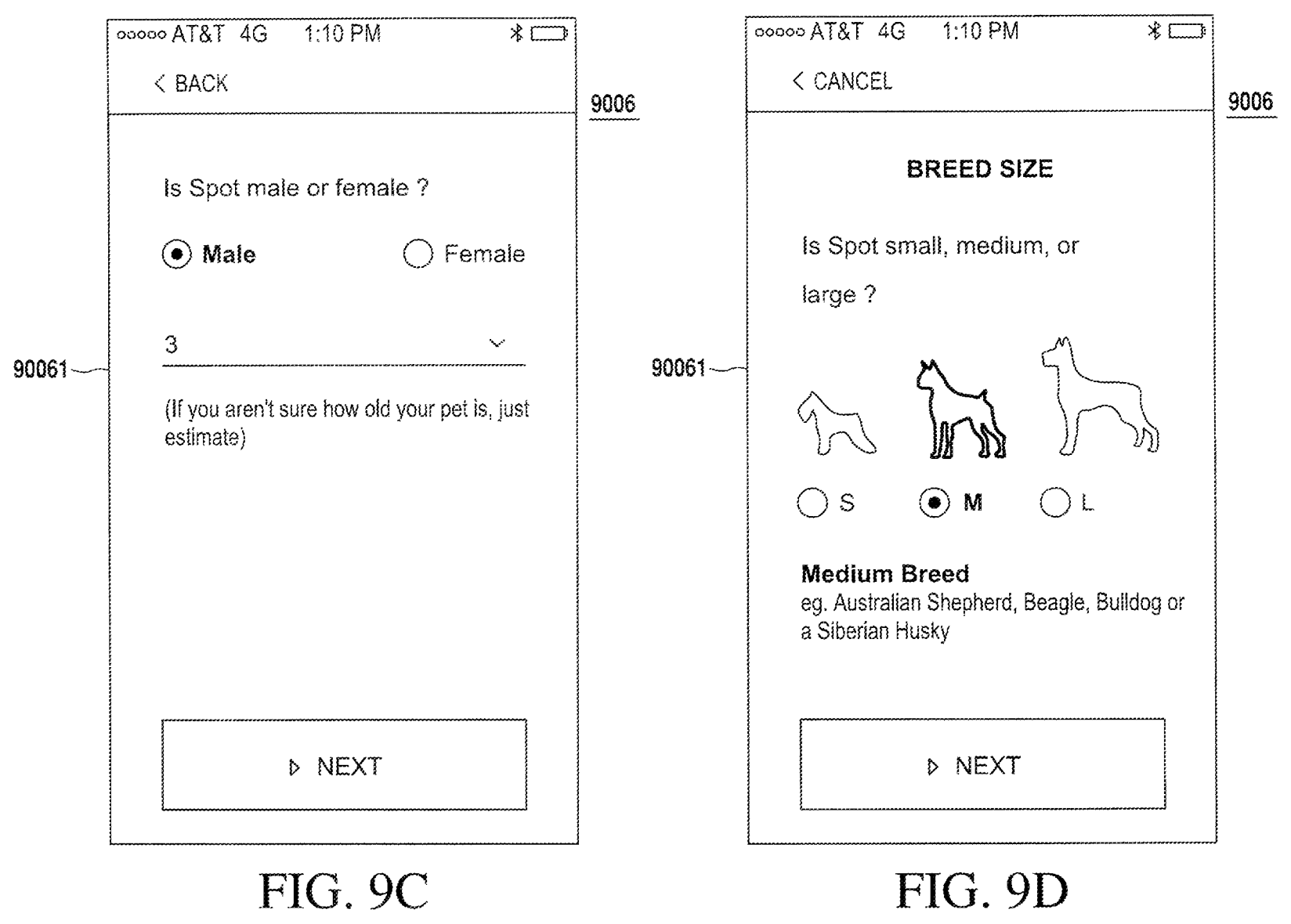

FIGS. 9A-9G illustrate an animal settings display of the mobile module.

FIGS. 12A-12C illustrate exemplary dashboard displays of the mobile module.

FIGS. 13A-13E illustrate exemplary data stream displays of the mobile module.

FIGS. 14A-14B illustrate exemplary notification displays of the mobile module.

FIGS. 15-23 illustrate data collected using exemplary systems and methods disclosed herein.

Figure 1:
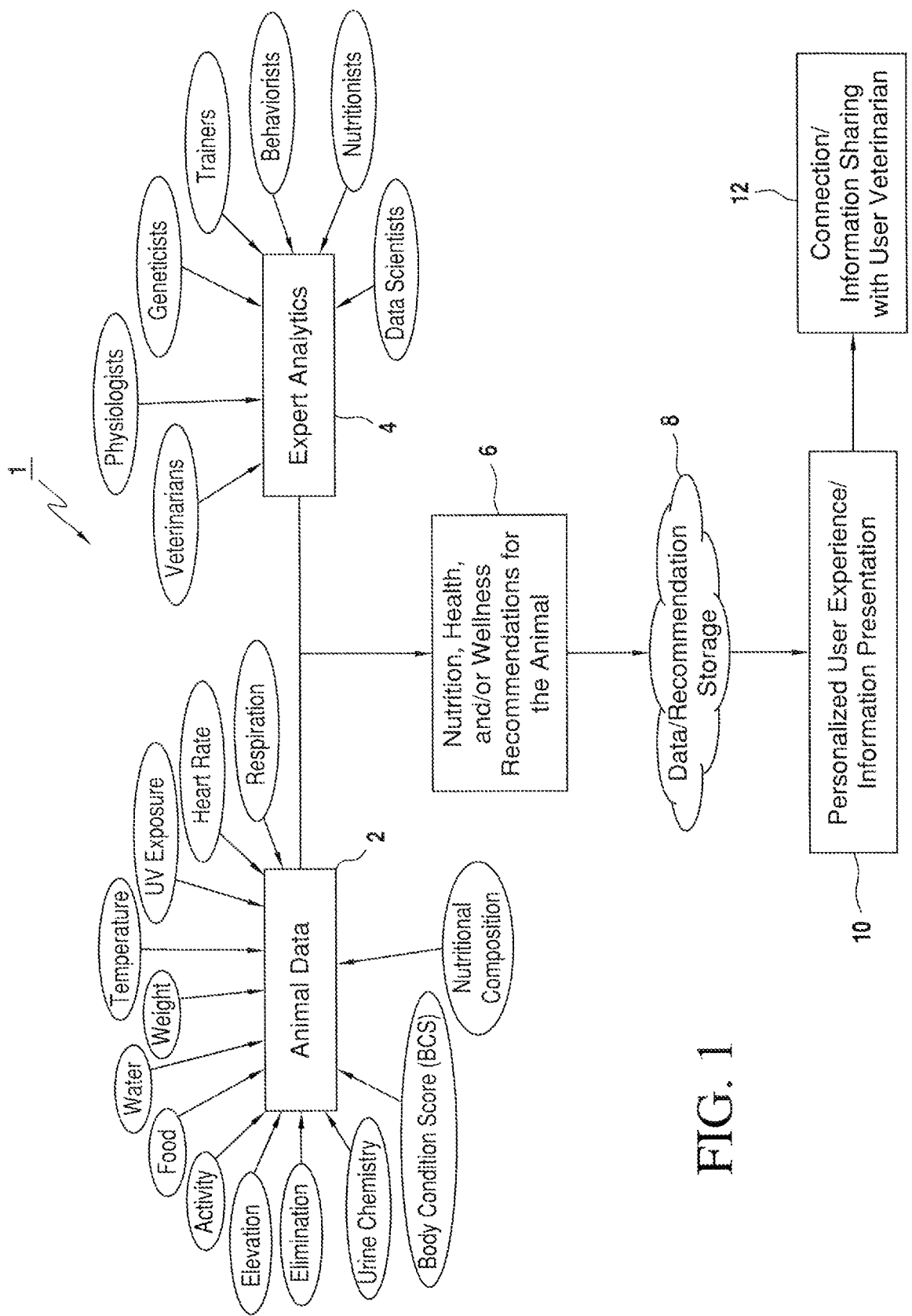
FIG. 1 illustrates a flowchart depicting exemplary embodiments used in preparing nutrition, health, and/or wellness recommendations for an animal in accordance with the present disclosure.

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denote the same elements.

The present disclosure has been described herein with reference to various exemplary embodiments. However, those skilled in the art will recognize that changes in modifications can be made to the exemplary embodiments without departing from the scope of the present disclosure. As used herein, the terms "comprises," "comprising," "includes," "including" and/or any other variation thereof, are intended to cover a non-exclusive inclusion, such that a system, process, method, article, and/or apparatus that comprises a list of elements does not include only those elements but can include other elements not expressly listed and/or inherent to such system, process, method, article, and/or apparatus. Further, no element described herein is required for the practice of the disclosure unless expressly described, e.g., as "essential" and/or "critical."

It must also be noted that, as used in this specification and the appended claims, the singular forms "a," "an" and "the" include plural referents unless the content clearly dictates otherwise.

Unless defined otherwise, all technical and scientific terms used herein have the same meaning as commonly understood by one of ordinary skill in the art to which the disclosure pertains. Although a number of methods and materials similar or equivalent to those described herein can be used in the practice of the present disclosure, certain preferred materials and methods are described herein.

The terms "first," "second," "third," "fourth," and the like in the description and in the claims, if any, are used for distinguishing between similar elements and not necessarily for describing a particular hierarchical, sequential, or chronological order. It is to be understood that the terms so used are interchangeable under appropriate circumstances such that the embodiments described herein are, for example, capable of operation in sequences other than those illustrated or otherwise described herein. Furthermore, the terms "comprise," "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein.

The terms "couple," "coupled," "couples." "coupling," and the like should be broadly understood and refer to connecting two or more elements or signals, electrically, mechanically, or otherwise. Two or more electrical elements may be electrically coupled, but not mechanically or otherwise coupled; two or more mechanical elements may be mechanically coupled, but not electrically or otherwise coupled; two or more electrical elements may be mechanically coupled, but not electrically or otherwise coupled. Coupling (whether mechanical, electrical, or otherwise) may be for any length of time, e.g., permanent or semi-permanent or only for an instant.

"Electrical coupling" and the like should be broadly understood and include coupling involving any electrical signal, whether a power signal, a data signal, and/or other types or combinations of electrical signals. "Mechanical coupling" and the like should be broadly understood and include mechanical coupling of all types. The absence of the word "removably," "removable," and the like near the word "coupled," and the like does not mean that the coupling, etc. in question is or is not removable.

DETAILED DESCRIPTION

In general, the systems and methods described herein involve the collection, analysis, and/or use of animal data to provide recommendations to the appropriate individuals (e.g., the owner/caretaker of the animal, veterinary personnel, etc.) on improving the overall nutrition, health, and wellness of the animal. As described herein, this data and its analysis can provide meaningful outcomes, insights, and advice about the animal that enable the individual to take recommended steps to improve the well-being of the animal. Through a variety of data collection techniques, discussed in detail below, various data regarding the animal can be generated and advice and recommendations can be communicated to the individual (or a group of individuals) to enhance the nutrition, health, and wellness profile of the animal.

A general framework of the systems and methods described herein is illustrated in FIG. 1. As shown, various animal data 2 is combined with expert analytics 4 to provide the nutrition, health, and/or wellness recommendations for the animal. Such data and recommendations can be stored 8 as described herein. Further, personalized user experiences and information presentation 10 are provided, e.g., by way of mobile modules in a mobile device, described below. This may also facilitate communication and information sharing 12 with health professionals. These various components are described in detail herein.

The data being acquired can be categorized into a range of data types. For instance, and as discussed in further detail below, the data can be provided by an individual (e.g., owner, caretaker, or veterinary personnel) based upon observation or personal knowledge, or may be derived from sensor or measurement technology placed on or around the animal or at locations the animal frequents (e.g., collar/leash, feeding/water stations, litter box, etc.); that is, the animal's environment. All data that is collected becomes resident in a common data structure (whether specific for the particular animal or across a broader spectrum of breeds or types of animal).

The data is analyzed using various algorithms, formulas, and calculations which, in essence, codify fundamental expert knowledge and applied science and research regarding health, nutrition, and wellness characteristics of animals, as well as predictive analytics, to create a system that is capable of continuously screening the new data and comparing it to historically derived data. In this way, important and meaningful outcomes, insights, and predictions can be identified and communicated to the relevant individuals.

It will be understood that various mathematical and algorithmic techniques, such as bivariate, multivariate and trend analysis, may be used in the analysis of the collected data. The combination of raw data collected over time and processed (derived) data accumulated over time for each animal can be used to develop a profile of nutrition, health, and/or wellness of the animal. Other examples may involve the use of various mathematical and algorithmic techniques, such as calculation of a covariance matrix and further application of Kalman filter for tracking the mean and covariance of an evolving process and atypical deviations from baselines. Other particular examples include causal conditional-type algorithms (e.g., if X then Y, where X is a cause of Y) and conditional probability-type algorithms (e.g., the probability of an event A that another event B has occurred). Further trend analysis can be used to assess whether an atypical variation is random or whether a trend is developing.

As noted, the algorithms are capable of continuously analyzing and assessing the data to produce predictive outcomes or results of the data analysis. The outcomes of these algorithmic and predictive analytics-based calculations may then be further screened and analyzed through expert knowledge and applied science to provide the nutrition, health, and/or wellness recommendations. It will be understood that some outcomes, and therefore recommendations, will be identified as being of higher importance than others. For example, outcomes, insights, and recommendations can range from irrelevant (and perhaps even unworthy of recommendation) to highly significant or critical (and perhaps worthy of an alert due to a high perceived risk to the animal). Many outcomes, insights, and recommendations will fall between these two extremes to provide meaningful advice to improve animal nutrition, health, and/or wellness. As will be discussed in further detail below, this may include recommended dietary changes based on a perceived health risk, suggested exercise plans based on perceived behavioral issues, and the like.

Outcomes and insights, and therefore recommendations, having little or no relevance may or may not be communicated to the appropriate individual. Those generating relevance, on the other hand, will be queued within the system for communication to the appropriate individual when/if appropriate. It will be understood that the individual may have the ability within the system to set threshold boundaries for the type and level of insights that they deem relevant or not. Outcomes, insights, and recommendations viewed as highly relevant or alert-worthy can be prioritized for immediate notification to the appropriate individual(s). It is also envisioned that multiple individuals could be notified of high relevance outcomes and recommendations (e.g., the animal owner/caretaker and the animal's veterinarian). Communications to the individual(s) may be made via software web-based or applications, e-mail, text, phone, or any other forms of electronic communication. For less than highly or materially relevant outcomes and recommendations, the individual(s) may receive a report from the system on a daily, weekly monthly, or yearly basis, or other relevant time frame.

Engagement of the individuals with and to the system can also be via web-based or software applications, e-mail, text, phone, and other relevant forms of electronic communication. This may also include interactive websites and social or peer-to-peer media applications and protocols. In this way, the individual can have the ability to tailor the user experience and preferences to fit their and the animal's needs. As discussed in further detail below, general categories of, feedback and/or recommendations include any number of nutrition, health, and wellness aspects of the animal. This may include, for example, general health characteristics and levels of risk; behavior aspects such as meaningful patterns and training/modification advice, including recommended changes in animal owner and/or animal behavior; activity aspects including meaningful patterns and modification advice; nutritional aspects including what and how to feed the animal and other general and specific advice and product recommendations for the animal; alerts and other notifications of any high-risk and/or critical outcomes and recommendations; and packaging of data and reports for use in conjunction with veterinary visits.

The systems and methods can also be configured to communicate with the appropriate individual, for example, by an alert or other message. The message or alert can correspond, for example, to a particular event or sequence of events observed by the collected data, or to the breach of a threshold(s) (either by reaching, exceeding, or falling below a threshold value(s) or condition(s)), whether predetermined or set by the user, for either collected or analyzed data. A message or alert can then be sent when the threshold data has been met. Communications of or about the message or alert may be sent to the individual(s) via software web-based or applications, e-mail, text, phone, or any other forms of electronic communication, and typically those with instant or relatively prompt access by the individual(s) such as phone, text, or e-mail.

It will be understood that any animal (and its owner) can be the intended beneficiary of the systems and methods described herein. Thus, the animal may be a companion animal such as dogs and cats, a farm animal such as cows, horses, swine, as well as birds and exotic animal such as zoo animals. In one particular embodiment, the animal is a dog or a cat. In another particular embodiment, the animal is a dog, a cat, or a multiple or combination thereof.

Animal Data

As discussed above, the outcomes and recommendations for improving or enhancing the nutrition, health, and or wellness of the animal are determined using various data 2 collected from the animal (FIG. 1). This can involve any one or more characteristics, or parameters, exhibited or possessed by the animal, or otherwise present in connection with the animal (such as environmental factors), In a particular embodiment, the foregoing analysis is performed on one or more of a health, diet, behavior, and environmental parameter of the animal.

Representative health parameters of the animal may include, for example, age; sex; gender; species or breed; body weight; body mass index (BMI); body composition; body condition score; body temperature; gait force; reproductive aspects (e.g., estrus, spay/neuter status, etc.); skin and coat condition; UV exposure; cardiovascular system (e.g., heart rate); respiratory system (e.g., respiration rate); gastrointestinal and kidney functions (e.g., fecal composition, urine chemistry, etc.); vision, cognitive health; combinations thereof; and the like.

Representative diet parameters of the animal may include, for example, food and water consumption including amounts and time of day; nutritional composition or profile of the food consumed; vitamin, supplement, and/or medication consumption; combinations thereof; and the like.

Representative behavior parameters of the animal may include, for example, activity profiles (e.g., calories burned, steps or distance traveled, intensity levels, changes in elevation, and time of day information); elimination activity including frequency, amount, and time of day information; vocalization (e.g., barking, meowing, and other sounds that can indicate animal dispositions); combinations thereof; and the like.

Representative environmental parameters of the animal may include, for example, weather information (e.g., air temperature, humidity, heat index, precipitation, etc.); location coordinates of animal; location coordinates of food/water/waste container/sleeping or resting locations/etc.; presence or absence of owner/caretaker at the location; presence or absence of children/elderly at the location; combinations thereof; and the like.

Taken as a whole, therefore, exemplary animal data may include, for example, any observable measure of the health or physical state of an animal determined by various means, and may be quantitative or qualitative, such as a weight of an animal, a weight of a waste deposited by an animal in a waste container, a body temperature of an animal, the weight of a platform before the presence of the animal is detected, the combined weight of the platform and the animal after the presence of the animal was detected, the weight of a platform after the departure of the animal was detected, the weight of the food consumed by the animal, the weight of the water consumed by the animal, the date when presence of the animal is detected, the time when presence of the animal is detected, the time when departure of the animal is detected, the duration of time between detection of the presence of the animal and the departure of the animal, a tip of the nose temperature of an animal, an ear temperature of an animal, an anal temperature of an animal, a height of an animal, a video or a picture or plurality thereof of an animal, a video or a picture or plurality thereof of animal body parts such as a face, an eye, eyes, parts of a skin, a paws, a video or a picture or plurality thereof of a waste container, a video or a picture or plurality thereof of a waste left by an animal, a video or a picture or plurality thereof of a substance in a waste container, a voice recording for the duration of animal's presence inside a waste container, a result of chemical, biological or biochemical analysis, the daily frequency with which presence of the animal is detected, the cumulative daily weight of the animal's waste, the cumulative daily weight of the food consumed by the animal, the cumulative daily weight of the water consumed by the animal, the average daily weight of the animal, the maximum and the minimum daily weight of the animal, the cumulative daily duration of time between each detection of the presence of the animal and the departure of the animal, the average, maximum and minimum rates of food and water consumption, expressed in weight of food and water consumed per unit of time, the cumulative daily number of times the presence of the animal is detected, the amount of time since the last time presence of the animal is detected, or the average daily time interval between instances where presence of animal is detected, and combinations and variations thereof.

In some embodiments, data on single or multiple parameters may be collected and analyzed. Thus, in one embodiment, the data collection and analysis may be performed on one of a health parameter, a diet parameter, a behavior parameter, or an environmental parameter. In another embodiment, the data collection and analysis maybe performed on two or more of a health parameter, a diet parameter, a behavior parameter and an environmental parameter Data collection and analysis of combinations of parameters may therefore also be performed.

For example, the data collection and analysis may be performed on health and diet parameters; heath and behavior parameters; health and environmental parameters; diet and behavior parameters; diet and environment parameters; behavior and environment parameters; health, diet, and behavior parameters; health, diet, and environmental parameters; health, behavior, and environment parameters; diet, behavior, and environmental parameters; and health, diet, behavior, and environmental parameters.

It will be understood that, for a multi-animal home or dwelling, it will in many respects be advantageous to have the ability to uniquely identify each animal and the parameters of the same that are collect and analyzed. In this way, the systems and methods have the ability to uniquely identify individual animals using the same system so that the data analysis is unique to each animal regardless of identity or even species (e.g., the possibility of having a single system in a home that captures data for both dogs and cats). For example, where multiple animals use a single waste container, each animal could be identified or distinguished based upon trends or observations (such as by weight, typical time of day of use, typical length of stay in the container, typical amount of waste deposited, etc.). By way of another example, where multiple animals use a single food and/or water container, each animal could be identified or distinguished based upon trends or observations (such as by weight, typical time of day of feeding/watering, typical length of stay at the food/water container, typical amount of food/water consumed, etc.). By way of further example, multiple measurement devices (e.g., including sensors) can be employed to accommodate multiple animals, such as distinct food/water containers, sleeping/resting locations, etc. In this way, the various systems and methods described herein can support any combination of single or multiple animals and single or multiple measurement/sensor devices.

Analysis of one or more of the foregoing parameters using collected data can thereafter be used to provide predictive outcomes and recommendations on nutrition, health, and/or wellness of the animal.

By way of example, and not by way of limitation, collected and analyzed data regarding animal heart rate can be indicative or otherwise informative of the animal's stress level; the animal's maximum/minimum heart rate; the animal's eating habits or food palatability; any pain experienced by the animal; the animal's excitement level; number of calories burned; comparative analysis of heart rate and activity level; aerobic capacity; joint/mobility issues; sleep/dream tracking; presence or absence of arrhythmia; post-surgery, post-illness or post-exercise return to baseline or normal; incident based anxiety (e.g., presence of the mailman or garbage truck); visitor/stranger acceptance; combinations thereof; and the like. These collected data and analysis may, in turn, lead to outcomes and recommendations regarding one or more of changes in environment; initiating, limiting, or increasing exercise protocols; administration or cessation of vitamins, supplements, or medication; initiating or modifying training protocols; nutritional/feeding changes; veterinary visits; combinations thereof; and the like.

By way of another example, and not by way of limitation, collected and analyzed data regarding food consumption of the animal (including amount and time-of-day patterns), can be indicative or otherwise informative of the animal's enjoyment or liking of the food; whether one animal is eating another animal's food (i.e., in a multi-animal house or dwelling); normal or irregular food ingestion rates (e.g., too fast or too slow); illnesses or gastrointestinal issues; seasonality issues (e.g., changes in patterns based on changes in temperature); nutrient deficiencies based on amount of food consumed; over/under feeding issues; hyper/hypophagia; combinations thereof; and the like. These collected data and analysis may, in turn, lead to outcomes and recommendations regarding one or more of changes in environment; initiating, limiting, or increasing exercise protocols; administration or cessation of vitamins, supplements, or medication; initiating or modifying training protocols; nutritional/feeding changes; veterinary visits; combinations thereof; and the like.

By way of another example, and not by way of limitation, collected and analyzed data regarding active minutes per day of the animal and the timing thereof can be indicative or otherwise informative of the animal's Circadian rhythms; aging; general health and fitness; metabolic disease; illness or malaise; anxious times or periods during the day; dementia or cognitive issues; joint or mobility issues; changes in life stage (puppy/adult/senior); effectiveness of recovery from illness/injury/surgery; effectiveness of diet and nutrition; multiple animal household relationships; combinations thereof; and the like. These collected data and analysis may, in turn, lead to outcomes and recommendations regarding one or more of changes in environment; initiating, limiting, or increasing exercise protocols; administration or cessation of vitamins, supplements, or medication; initiating or modifying training protocols; nutritional/feeding changes; veterinary visits; combinations thereof; and the like.

By way of another example, and not by way of limitation, collected and analyzed data regarding number of steps taken per day by the animal can be indicative or otherwise informative of the time of day when calorie burn is elevated or decreased; the social ability of the animal; the total motion of the animal; anxiety level of the animal (e.g., pacing while the owner/caretaker is away); speed and changes in speed over time that can indicate stiffness or joint/mobility issues; dementia and cognitive health; illness or injury in limbs; incident based anxiety (e.g., presence of the mailman or garbage truck); Circadian rhythms; waking/sleeping schedules; post-surgery, post-illness, or post-exercise return to baseline or normal; rate of aging or relative age of animal, basal metabolism; need for more physical activity; need for increased or decreased activity or exercise; combinations thereof; and the like. These collected data and analysis may, in turn, lead to outcomes and recommendations regarding one or more of changes in environment; initiating, limiting, or increasing exercise protocols; administration or cessation of vitamins, supplements, or medication; initiating or modifying training protocols; nutritional/feeding changes; veterinary visits; combinations thereof; and the like.

By way of another example, and not by way of limitation, collected and analyzed data regarding the number of calories burned per day by the animal can be indicative or otherwise informative of the animal's metabolism; the calories required by the animal and the amount of food/treats to provide; particular type of food/treats to give the animal (e.g., performance or weight management); feed/treating times of day; activity when owner/caretaker is away; joint/mobility issues; energy expenditure; dementia or cognitive issues; increased water needs; combinations thereof; and the like. These collected data and analysis may, in turn, lead to outcomes and recommendations regarding one or more of changes in environment; initiating, limiting, or increasing exercise protocols; administration or cessation of vitamins, supplements, or medication; initiating or modifying training protocols; nutritional/feeding changes; veterinary visits; combinations thereof; and the like.

By way of another example, and not by way of limitation, collected and analyzed data regarding the body weight of the animal can be indicative or otherwise informative of changes over time (e.g., over/under weight, over/under feeding; protein levels; by-breed comparisons; onset of illness; gastrointestinal issues; diseases, conditions, or other health issues (e.g., thyroid problems, tumors, etc.); energy balance; need to change foods based on life stage (e.g., when weight plateaus in puppies, begins declining in older dogs, etc.); effectiveness of weight loss/gain programs or diets; daily caloric needs; resting metabolism; water/food intake; combinations thereof; and the like. These collected data and analysis may, in turn, lead to outcomes and recommendations regarding one or more of changes in environment; initiating, limiting, or increasing exercise protocols; administration or cessation of vitamins, supplements, or medication; initiating or modifying training protocols; nutritional/feeding changes; veterinary visits; combinations thereof; and the like.

By way of another example, and not by way of limitation, collected and analyzed data regarding water consumption of the animal can be indicative or otherwise informative of animal hydration levels/status (e.g., as compared to body weight to determine if hydration levels are adequate); dehydration/salt content; diabetes or the onset thereof; the animal's meeting of hydration requirements; fluctuations in water consumption; the water's use as a media for delivery of supplements or medication; elimination behaviors; anxiety, stress, or boredom; risks of renal crystals; when water source/container needs replenished; seasonality; risks of renal failure; drinking frequency and changes over time; time-of-day patterns; cleanliness of water source/container; food consumption and type; potential consumption of inappropriate food/items; combinations thereof; and the like. These collected data and analysis may, in turn, lead to outcomes and recommendations regarding one or more of changes in environment; initiating, limiting, or increasing exercise protocols; administration or cessation of vitamins, supplements, or medication; initiating or modifying training protocols; nutritional/feeding changes; veterinary visits; combinations thereof; and the like.

In addition, collected data and analysis on certain parameters can be indicative of a number of particular issues for the animal. For example, one or more changes in animal activity; changes in rest periods/intensity; changes in food/water consumption; changes in steps taken; changes in weight; irregular elimination behavior; body temperature; results of blood, urine, and/or stress tests; and combinations thereof, may be indicative or otherwise informative of certain cancers in the animal. By way of another example, changes in food/water consumption; changes in weight; seasonality; abnormal scratching; hair loss; changes in appearance; and combinations thereof, may be indicative or otherwise informative of allergies in the animal (whether food allergies, environmental allergies, or bacterial/viral allergies). By way of another example, changes in activity; number of steps (e.g., pacing); heart rate; increased water intake and decreased food intake; vocalization (e.g., whining); and combinations thereof, may be indicative or otherwise informative of anxiety, stress, or boredom in the animal. By way of another example, the age; breed; reproductive aspects (e.g., estrus, spay/neuter status, etc.); rest patterns; activity patterns including number of steps and calories burned; changes in caloric intake; changes in feeding patterns; and combinations thereof, may be indicative of the life stage (or a change thereof) of the animal. By way of another example, increases in water intake; increases or decreases in body weight; the age and breed of the animal; urine color; decreases in activity; food type; and combinations thereof, may be indicative of diabetes in the animal. These collected data and analysis may, in turn, lead to outcomes and recommendations regarding one or more of changes in environment; initiating, limiting, or increasing exercise protocols; administration or cessation of vitamins, supplements, or medication; initiating or modifying training protocols; nutritional/feeding changes; veterinary visits; combinations thereof; and the like.

Differing combinations of collected data and analysis on certain parameters can also be indicative of multiple issues for the animal. By way of example, the combination of heart rate and body weight data, may be indicative or otherwise be informative of hypertension; anorexia; hyperfusia; fitness; exertion; anxiety, stress, or boredom of the animal. By way of another example, the combination of heart rate, body weight, and body composition data may be indicative or otherwise informative of aging; obesity; training deficiencies; fitness issues; metabolic needs; and nutritional needs of the animal. By way of another example, the combination of heart rate, body weight, and vocalization data can be indicative or otherwise informative of anxiety, stress, or boredom, or physical or emotional distress of the animal. By way of another example, the combination of weight, body temperature, heart rate, and respiration data can be indicative or otherwise informative of the overall health and well-being of the animal. By way of another example, increased water intake of the animal can be indicative or otherwise informative of anxiety, stress, or boredom; urinary tract issues; increased calcium levels; liver disease; hyperthyroidism; and acute and chronic renal issues of the animal. By way of another example, the number of calories burned per day; resting minutes per day; steps taken per day; and location of the animal can be indicative or otherwise informative of weight and diet issues; metabolic issues; activity patterns; pre-disease status; baseline and adjusted fitness and activity levels; multi-animal household issues of the animal; dementia and cognitive issues; and the general well-being of the animal. By way of another example, food intake, water intake, body weight and activity levels can be indicative or otherwise informative of body mass indications; elimination behavior; palatability of food; food/water container issues;

weight gain/loss (e.g., due to Addison's disease, hypothyroidism); early disease state or onset; advanced disease states; stress patterns; renal issues; arthritis; joint/mobility issues; training deficiencies; aging; and life stage changes of the animal. By way of another example, food intake, water intake, number of steps taken, body weight, and heart rate can be indicative or otherwise informative of energy balance (e.g., by breed and/or by life stage); baseline and adjusted happiness/contentment/satisfaction levels; changes in energy levels; disease status; food suitability and palatability; and anxiety, stress, or boredom of the animal. By way of another example, food intake, water intake, activity level, body weight, age, heart rate, and body temperature can be indicative or otherwise informative of nutrition/malnutrition issues; cancers; renal issues; hyperthyroidism; and infectious diseases of the animal. By way of another example, body weight, age, breed, activity levels, glucose levels, and water intake can be indicative or otherwise informative of diabetes or onset thereof, and musculoskeletal diseases such as hip dysplasia and osteoarthritis. These collected data and analysis may, in turn, lead to outcomes and recommendations regarding one or more of changes in environment; initiating, limiting, or increasing exercise protocols; administration or cessation of vitamins, supplements, or medication; initiating or modifying training protocols; nutritional/feeding changes; veterinary visits; combinations thereof; and the like.

Still further examples of relevant data and analysis include one or more of the following: the combination of heart rate and respiration rate of the animal; urine chemistry as an indicator of physiological changes within the animal over time; body condition scoring, e.g., whereby animal owners rate the body condition of the animal (including, for example, providing photographs of the animal when creating animal profiles in the mobile modules discussed below); nutritional composition/profile of the animal's food (including, for example, providing photographs of the bar codes or other information on the food they feed their animals, such that databases can be accessed to provide the label declaration nutrition analysis on such products) which can provide insights into the animal's consumed nutrition levels (e.g., for comparing different manufacturer's products, batch analysis, etc. to determine true caloric intake and nutrition composition levels in the animal); UV exposure and related diseases; elevation (e.g., going up/down steps, climbing hills, etc.) and normal rate of standing/sitting/laying changes over time as a predictor of early onset of joint health problems; animal body temperature versus ambient temperature around the animal. Still other examples of data include linking to weather sites, correlating behavior of individual and multiple pets to earthquake monitoring data, using facial recognition as a way to identify which animal is using a device (who is eating/drinking, using the scale, using the litter box, etc.), GPS or other location-monitoring technologies to pinpoint location of the animal (e.g., in/out of house, etc.).

Expert Analytics

In addition to the animal data 2, the systems and methods disclosed herein utilize expert analytics 4 to provide more accurate and/or meaningful recommendations regarding animal health and/or wellness. The techniques of the present disclosure thus provide the capability to extract informative data from the raw data, which is then collected and analyzed by relevant human expert analysis. As depicted in FIG. 1, for example, among the various experts are veterinarians, physiologists, geneticists, trainers, behaviorists, nutritionists, and data scientists.

Expert review in real-time or over an extended period of time is used to determine the optimum therapeutic/nutritional index or recommendation for that particular animal or animal class. For example, if a threshold level or baseline of the collected data discussed above is breached, appropriate action can be recommended by the expert and taken by the animal owner or other individual. An appropriate action could be alerting the owner/individual, stopping or starting certain medication or the like. As will be understood, the appropriate action or recommendation for an animal would be decided based on the collected data and the expert's experience and judgment for that particular animal or class of animals. In will also be understood that the expert analysis can occur as a one-time exercise using the data set derived from the animal, and/or as an ongoing exercise using clinical studies and/or existing clinical information, for instance.

Thus, the expert has the ability to draw upon his or her own experience, and also has access to additional information, e.g., historical information within the system memory, historical information about the particular animal from one or more accessible databases, and information about a plurality of animals from still other databases. The expert(s) may have a variety of control-sharing relationships with the systems and methods described herein from complete control to provide insight or recommendations, or a sharing arrangement in which, for example, multiple experts are able to provide insight and recommendations in order to influence treatment or actions taken by the user/animal owner. Further, the experts are able in some embodiments to prepare and send analytics-generated messages (e.g., pet health and wellness information) and system information messages within the system (e.g., via the mobile module discussed in detail below).

Animal Data Collection

The aforementioned animal health, behavior, and/or environmental data can be collected or derived and analyzed using a number of techniques and/or sensing/monitoring devices.

The data may be derived from qualitative observations by animal owners/caretakers or periodic veterinary examinations. This may include observed and recorded changes in weight, activity, food and/or water consumption, elimination frequency and consistency, and the like, as compared to prior observations and recordation of the same. Additionally, or alternatively, the data can be collected on an automated basis, either continuously or and periodic intervals, using one or more sensors associated with, for example, the animal itself or locations frequented by the animal (e.g., food/water containers, waste containers, frequent sleeping/resting locations, etc.) and measuring devices.

For example, data can be continuously captured during the entire duration of the animal's activity inside a waste container, during food or water consumption, sleep or rest until the animal moves away effectively disengaging measurement. Data can also be captured by periodically sampling a sensor or sensors, such as weight, pressure or force sensor or sensors (such as strain gauges, load cells, piezo sensors, etc.) and converting a contiguous (analog) electrical signal into a digital data.

Thus, a variety of sensors and measuring devices may be utilized in the data collection step. Exemplary sensors include, but are not limited to, accelerometers (single axis or multi-axis), gyroscopes, weighing scales, weight transducers, force transducers, displacement transducers, orientation sensors (e.g., compasses), pressure transducers, weight sensors, force sensors, pedometers, displacement sensors, pressure sensors, load cells, photographic cameras, video cameras, camcorders, RF location beacons, contact thermometers, non-contact thermometers, such as infrared thermometers, laser thermometers, infrared pyrometers, laser pyrometers, litters or litter additives that change their properties, such as color, odor, outgassing, fluorescence, luminescence, when come in contact with animal waste, either urine or excrements. Other sensors may also be used to determine an animal's presence or absence at a particular location or height, such as optical sensors, optical reflecting sensors, LED/photodiode pair optical sensors, LED/phototransistor pair optical sensors, laser diode/photodiode pair optical sensors, laser diode/phototransistor pair optical sensors, optocouplers, optical fiber coupled optical sensors, magnetic sensors, weight sensors, force sensors, displacement sensors, pressure sensors (relative/differential or absolute), various proximity sensors, such as inductive proximity sensors, magnetic proximity sensors, capacitive proximity sensors, global positioning system (GPS) devices, a global navigation satellite system (GNSS) devices, and/or a combination thereof. In general, all types of sensors and sensing techniques, whether now known or later developed, that are capable of generating data which is representative of motion and/or presence of an animal are intended to fall within the scope of the present disclosure.

Particular sensor and measuring devices and methods and systems for using the same in the collection of physiological and behavioral animal data, and the storage and transmittal of the same, are described in U.S. Pub. Nos. 2011/0315084; 2012/0299731; 2013/0073254; and 2013/0192526 (each of which are hereby incorporated by reference in their entirety).

For example, U.S. Pub. No. 2011/0315084 provides a cat litter box including monitoring system that detects a cat's behavior relative to the cat litter box. The litter box includes an identification system, such as a radio-frequency identification (RFID) system, in order to track individual cat activity. As part of the monitoring, data with important health implications, such as average trips to the litter box per a set period of time can be stored and transmitted. User alerts may be sent if there is a significant change in behavior, such as no visits to the litter box in a set period of time (e.g., 24 hours). The monitoring system may also include a weight sensor, such that the litter box store and transmit historical weight information on the cat(s) that use it. User alerts can be sent if a weight change violates a range. The weight sensor can also be used for the identification of individual cats and/or for the determination of the type and quantity of waste left by a cat in the litter box. Health data can be generated as an alert to potential underlying health problems, such as kidney disease or diabetes, historical weight information as an early indicator of an underlying disease, or lack of litter box activity which could indicate isolation from the litter box (e.g., locked in a separate area of a home, sick and/or injured, etc.).

By way of another example, U.S. Pub. No. 2012/0299731 provides a waste container or perch (e.g., for avian animals) comprising a scale and other sensors to measure and/or determine characteristics of the animal while it is disposed in the container or on the perch. Feeding and water stations comprising scales and other sensors for measuring and/or determining characteristics of the animal are also disclosed.

By way of another example, U.S. Pub. No. 2013/0073254 provides portable monitoring devices capable of monitoring, calculating, determining and/or detecting energy and/or calorie "burn" due to physical activity. The portable monitoring device is affixed to the user during operation, and the housing of the device is of a physical size and shape that facilitates coupling to the user via a mechanism (for example, a clip, strap and/or tie) that facilitates coupling or affixing the device to the user and allows the user to perform normal or typical user activities without hindering the user from performing such activities.

By way of another example, U.S. Pub. No. 2013/0192526 provides a rover unit (i.e., a pet collar, harness, or clothing) carried by the animal capable of detecting and transmitting physiological conditions and actions of the animal.

Figure 2:
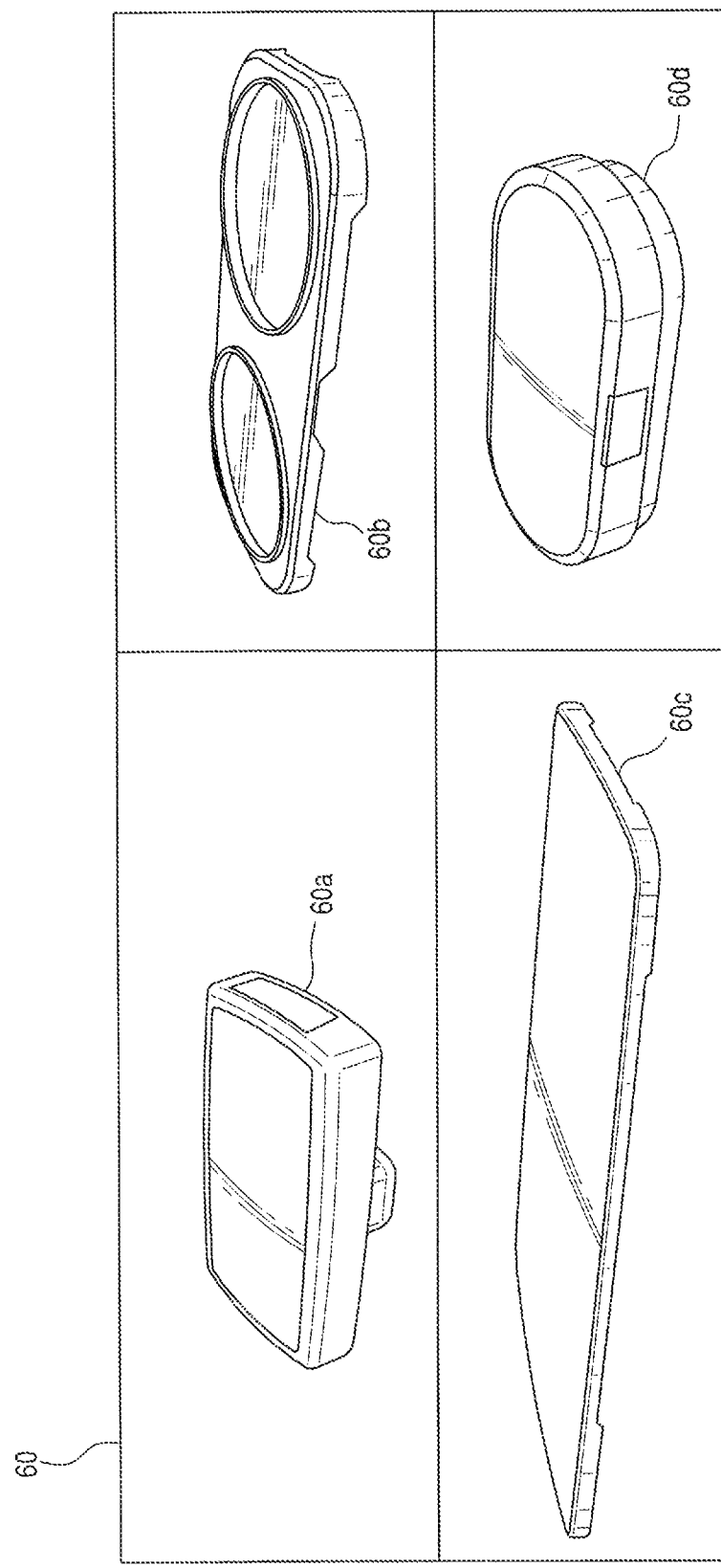
FIG. 2 illustrates exemplary animal sensing and/or monitoring devices for use in the systems and methods described herein.

Certain exemplary embodiments of sensing/measuring devices 60 are depicted in FIG. 2. For instance, the device 60 may comprise an on-animal monitor 60a, which may be coupled to the collar, leash, or other accessory of the animal. On-animal devices of this type may be configured to measure, among other things, animal surroundings, animal activity, body temperature, ambient temperature, elevation/altitude changes, UV exposure, and the like. Another type of device 60 comprises a nutrition/hydration station 60b, which may include one or more food and water receptacles. Devices of this type may be configured to monitor, among other things, food and water mass consumption, feeding/drinking event duration, eating behavior patterns, and the like. Another type of device 60 comprises a weight monitor 60c. Devices of this type can be placed under the animal's kennel or sleeping/resting location, for example, to provide real-time weight tracking. Another type of device 60 comprises a litter box activity monitor 60d, which may be positioned on or near the animal's waste container. Devices of this type can be configured to monitor, among other things, activity frequency and duration of use of the waste container. Combinations of devices 60a, 60b, 60c, and/or 60d may be used to provide more complete packages of animal data 2. As will be understood, these exemplary devices can therefore be equipped one or more of the various sensors discussed above.

Analytical Techniques and Systems

With respect to data analysis, this may include the many types of software development methodologies and tools/program languages that exist, such as cloud-based data architectures, "Big Data" analytics systems and methods (e.g., via Amazon's Elastic MapReduce (EMR) and/or Google's I/O), and HTML based applications (e.g., HTML5). These methodologies, tools, and programs may be executed alone or, more preferably, in conjunction with one or more of (1) inventor's and applicant's expert knowledge in animal nutrition, health, and wellness; (2) expert knowledge of other individuals and groups in practice and academia; (3) expert knowledge of data scientists and research and development individuals and groups to create additional, or alternative, predictive analytics algorithms based on the treatment of the data collected on individual animals (i.e., data scientists associated with the applicant, as well as, other third party groups and partners); and (4) emerging machine-learning technologies that are capable of automating data analysis using high-speed processors to identify significant trend and insights within the data set.

As those skilled in the art will appreciate, the various system computing components discussed herein can include one and/or more of the following: a host server and/or other computing systems including a processor for processing digital data; storage or memory coupled to said processor for storing digital data; an input digitizer coupled to the processor for inputting digital data; an application program stored in said memory and accessible by said processor for directing processing of digital data by said processor; a display device coupled to the processor and memory for displaying information derived from digital data processed by said processor; and a plurality of databases. The computing systems can include an operating system (e.g., OS/360, MVS, Windows NT, 95/98/2000/XPNista, OS2, UNIX, Unix-like, TPF, Linux, Solaris, MacOS, Mac OS X, AIX, Google Chrome OS, Plan 9, Android, iOS, Blackberry, Windows Phone, etc., and the like) as well as various conventional support software and drivers typically associated with computers and mobile/smart phone devices.

As noted above, systems for use in connection with the methods described herein can include storage devices for storing the collected and/or analyzed data. Such storage devices may include, for example, memory devices, data storage devices and a combination thereof such as memory chips, semiconductor memories, Integrated Circuits (IC's), non-volatile memories or storage device such as flash memories, Read Only Memories (ROMs), Erasable Read Only Memories (EROMs), Electrically Erasable Read Only Memories (EEROMs), Erasable Programmable Read Only Memories (EPROMs), Electrically Erasable Programmable Read Only Memories (EEPROMs), an Electrically Erasable Programmable Read Only Memory (EEPRO), volatile memories such as Random Access Memories (RAMs), Static Random Access Memories (SRAMs), Dynamic Random Access Memories (DRAMs), Single Data Rate memories (SDRs), Dual Data Rata memories (DDRs), Quad Data Rate memories (QDR's), microprocessor registers, microcontroller registers, CPU registers, controller registers, magnetic storage devices such as magnetic disks, magnetic hard disks, magnetic tapes, optical memory devices such as optical disks, compact disks (CDs), Digital Versatile Disks (DVDs), Blu-ray Disks, Magneto Optical Disks (MO Disks), USB flash memory or other external memory devices (e.g., portable hard drives), and/or a combination thereof.

Systems may also include a processor configured to analyze collected data. Exemplary processors include, for example, electronic circuits, systems, modules, subsystems, sub modules, devices and combinations thereof, such as Central Processing Units (CPUs), microprocessors, microcontrollers, processing units, control units, tangible media for recording and/or a combinations thereof. It will be understood that the sensors and measuring devices, storage devices, and processors may be assembled as a single unit, or as multiple, standalone devices capable of communication with one another.

It will also be appreciated that the present disclosure can be embodied as a method, a system (e.g., a data processing system), a device for data processing, a computer program product, and/or a communications device. Accordingly, the present disclosure can take the form of an entirely software embodiment, an entirely hardware embodiment, and/or an embodiment combining aspects of both software and hardware. Furthermore, the present disclosure can take the form of a computer program product on a computer-readable storage medium having computer-readable program code means embodied in the storage medium. Any suitable computer-readable storage medium can be utilized, including hard disks, CD-ROM, optical storage devices, magnetic storage devices, and/or the like.

Mobile Monitoring Systems

Figure 3:
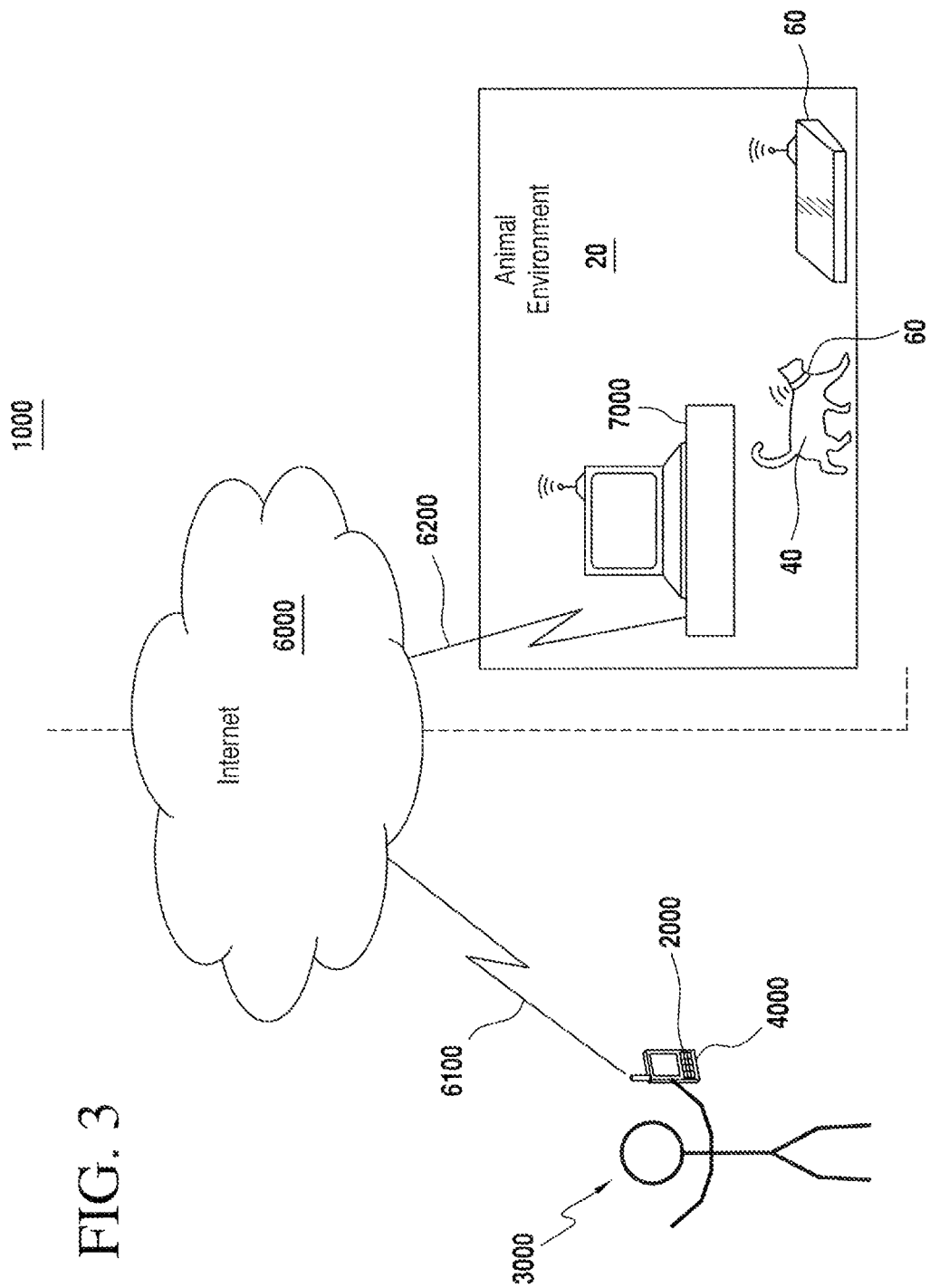
FIG. 3 illustrates a diagram of a mobile system comprising a mobile module for permitting a user to communicate remotely with the animal sensing and/or monitoring devices.

Turning again to the drawings, FIG. 3 illustrates a diagram of mobile animal monitoring system 1000, comprising mobile module 2000 for permitting user 3000 to receive information regarding an animal 40 in its environment 20. As shown, the animal environment includes one or more sensor/measuring devices 60 as described herein. In the present embodiment, mobile module 2000 is implemented via mobile device 4000, which is associated with user 3000 and can be, for instance a portable or handheld electronic device such as a cellular phone, a smartphone, a personal digital assistant (PDA), and/or a tablet device. For instance mobile device 400 can be an electrical device manufactured by Research in Motion Limited (e.g., a Blackberry® device), Palm, Inc. (e.g., a Palm® device), Apple Computer, Inc. (e.g., an iPod® MP3 player, an iPod Touch® device, an iPad® device, and/or an iPhone® device), and/or Samsung Electronics Co. Ltd. (e.g., a Galaxy® device). In other examples, mobile device 400 can be a portable computer (e.g., a laptop or similar device such as those manufactured by the aforementioned, or other, companies).

Mobile device 4000 can be configured to establish a wireless connection 6100 with Internet 6000. Similarly, the animal data collection device(s) 60 can be configured to communicate via Internet 6000 through connection 6200, which may be wired or wireless. Thus, mobile device 400 and data collection device 60 can communicate via Internet 6000. In some examples, a portion of connection 6100 and/or of connection 6200 can be carried out via a network configured for a wireless and/or cellular standard such as WiFi (IEEE 802.11a/b/g/n), WiPAN (IEEE 802.15, Bluetooth®), W-CDMA (Wideband Code Division Multiple Access), HSPA (High Speed Packet Access), EDGE (Enhanced Data Rate for GSM Evolution), WiMAX (Worldwide Interoperability for Microwave Access), LTE (Long Term Evolution), etc.

Figure 4:
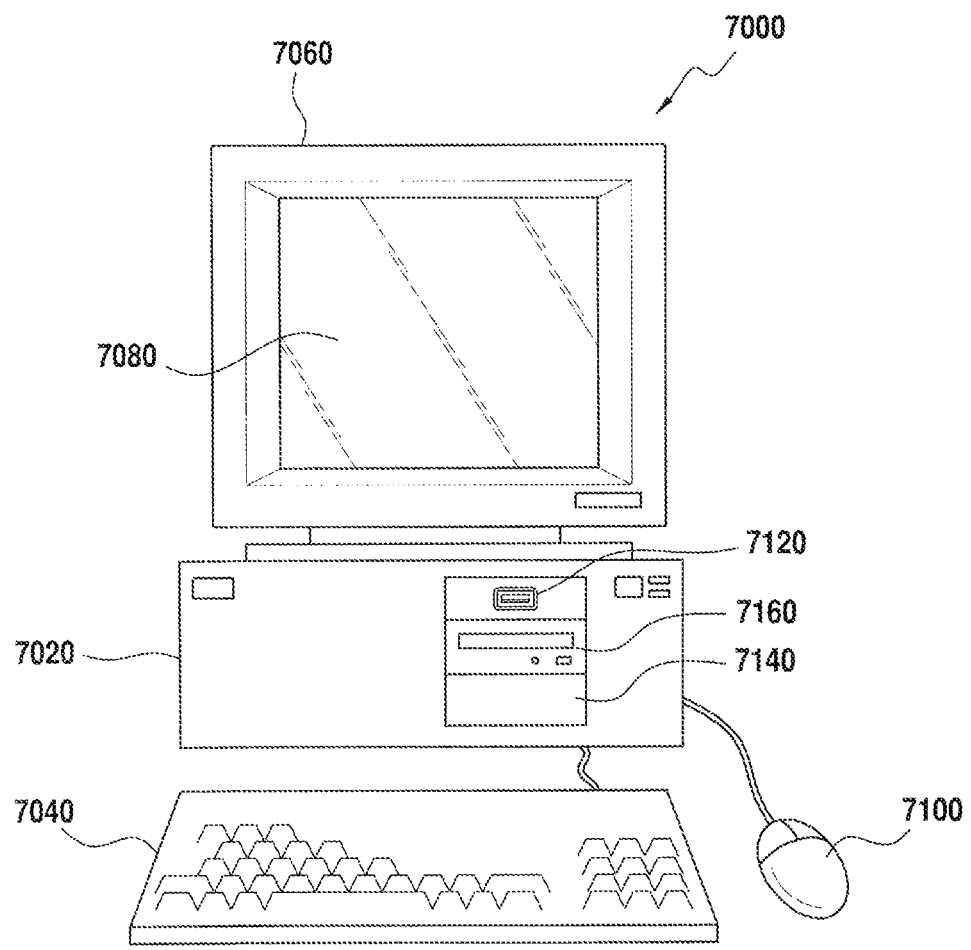
FIG. 4 illustrates a computer suitable for implementing an embodiment of the monitoring system.
Figure 5:
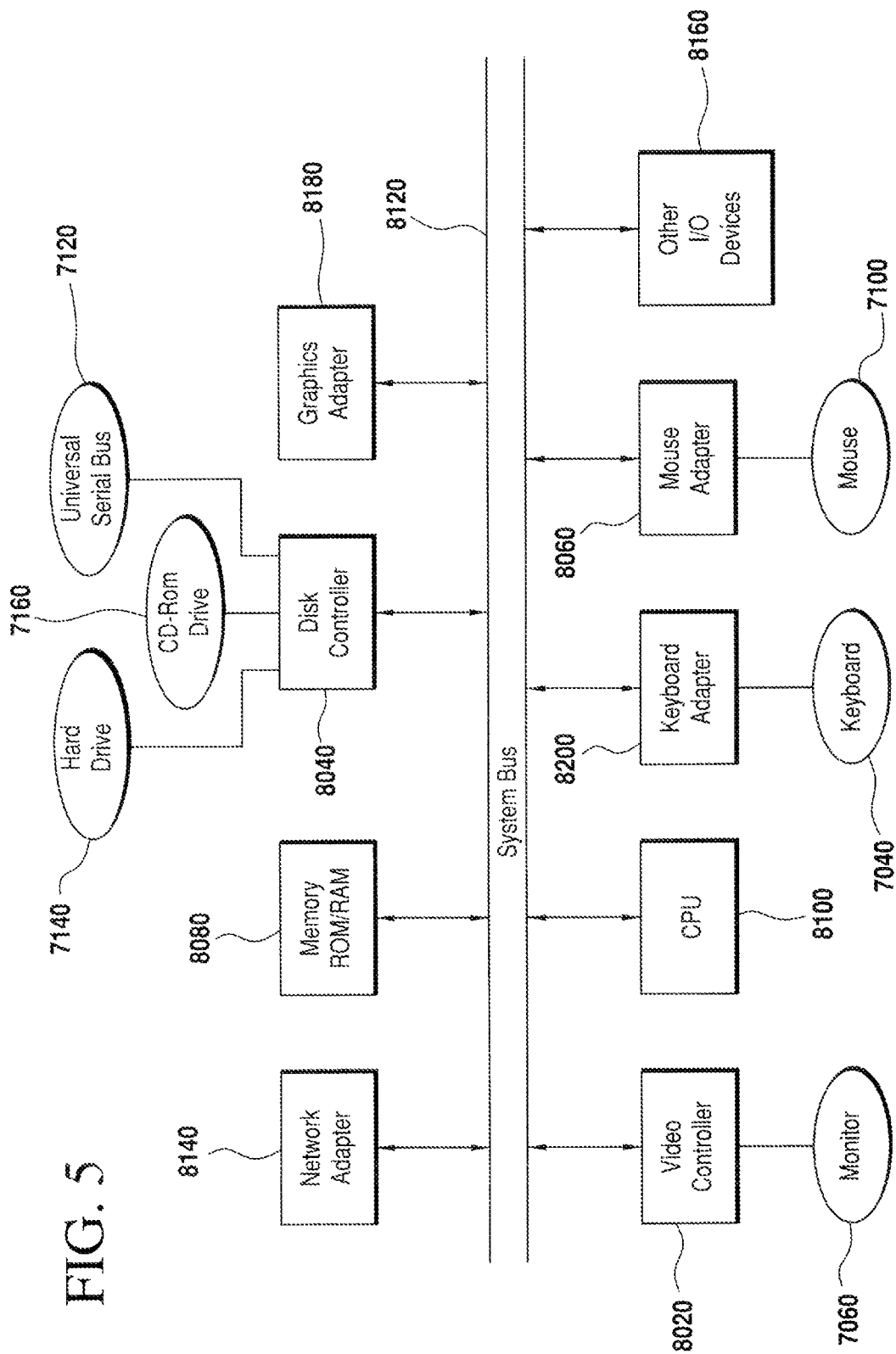
FIG. 5 illustrates a representative block diagram of the elements of the computer of FIG. 4.

FIG. 4 illustrates a computer 7000 suitable for implementing an embodiment of mobile monitoring system 1000. Computer 7000 includes a chassis 7020 containing one or more circuit boards (not shown), a USB (universal serial bus) port 7120, a Compact Disc Read-Only Memory (CD-ROM) and/or Digital Video Disc (DVD) drive 7160, and a hard drive 7140. A representative block diagram of the elements included on the circuit boards inside chassis 7020 is shown in FIG. 5. A central processing unit (CPU) 8100 is coupled to a system bus 8140 in FIG. 5. In various embodiments, the architecture of CPU 8100 can be compliant with any of a variety of commercially distributed architecture families.

System bus 8120 also is coupled to memory 8080 that includes both read only memory (ROM) and random access memory (RAM). Non-volatile portions of memory 8080 or the ROM can be encoded with a boot code sequence suitable for restoring computer 7000 (FIG. 4) to a functional state after a system reset. In addition, memory 8080 can include microcode such as a Basic Input-Output System (BIOS). In the depicted embodiment of FIG. 5, various I/O devices such as a disk controller 8040, a graphics adapter 8180, a video controller 8020, a keyboard adapter 8200, a mouse adapter 8060, a network adapter 8140, and other I/O devices 8160 can be coupled to system bus 8120. Keyboard adapter 8200 and mouse adapter 8060 are coupled in the present example to keyboard 7040 and mouse 7100, respectively, of computer 7000. While graphics adapter 8180 and video controller 8020 are indicated as distinct units in FIG. 5, video controller 8020 can be integrated into graphics adapter 818, or vice versa in other embodiments. Video controller 8020 is suitable for refreshing monitor 7090 to display images on a screen 7080 of computer 7000. Disk controller 8040 can control hard drive 7140, USB port 7120, and/or CD-ROM or DVD drive 7160. In other embodiments, distinct units can be used to control each of these devices separately.

Network adapters 8200 can be coupled to one or more antennas. In some embodiments, network adapter 8200 can be configured for WiFi communication (IEEE 802.11), and/ or may be part of a WNIC (wireless network interface controller) card (not shown) plugged or coupled to an expansion port (not shown) in computer 7000. Such WNIC card can be a wireless network card built into internal computer 7000 in some examples. A wireless network adapter can be built into internal client computer 7000 by having wireless Ethernet capabilities integrated into the motherboard chipset, or implemented via a dedicated wireless Ethernet chip, connected through the PCI (peripheral component interconnector) or a PCI express bus. In the same or other embodiments, network adapters 8200 can be configured for communication via other wireless protocols, such as via WPAN, W-CDMA, HSPA, EDGE, WiMAX, LTE, or others. In other embodiments, network adapter 820 can be a wired network adapter.

Although other components of computer 7000 are not shown, such components and their interconnection are well known to those of ordinary skill in the art. Accordingly, further details concerning the construction and composition of computer 7000 and the circuit boards inside chassis 7020 need not be discussed herein.

When computer 700 is in operation, program instructions stored on hard drive 714, on memory 808, on a USB drive in USB port 712, and/or on a CD-ROM or DVD in CD-ROM and/or DVD drive 916, can be executed by CPU 1010 (FIG. 5). Such program instructions may correspond to an operating system (OS) such as an Apple OS, a Microsoft Windows OS, a Linux OS, and/or a UNIX OS, among others. A portion of such program instructions can be suitable for implementing or carrying out the systems and methods described herein.

In the present example of FIG. 3, one or more sensing/measurement devices 60 are coupled to computer 7000. Alternatively, the devices 60 may be coupled to the Internet 6000 (not shown) and the mobile module 2000, in which case the computer 7000 is not necessary. Mobile module 2000 can be configured to communicate with computer 7000 (or device(s) 60) to permit user 3000 to access information collected by the device 60.

Figure 6:
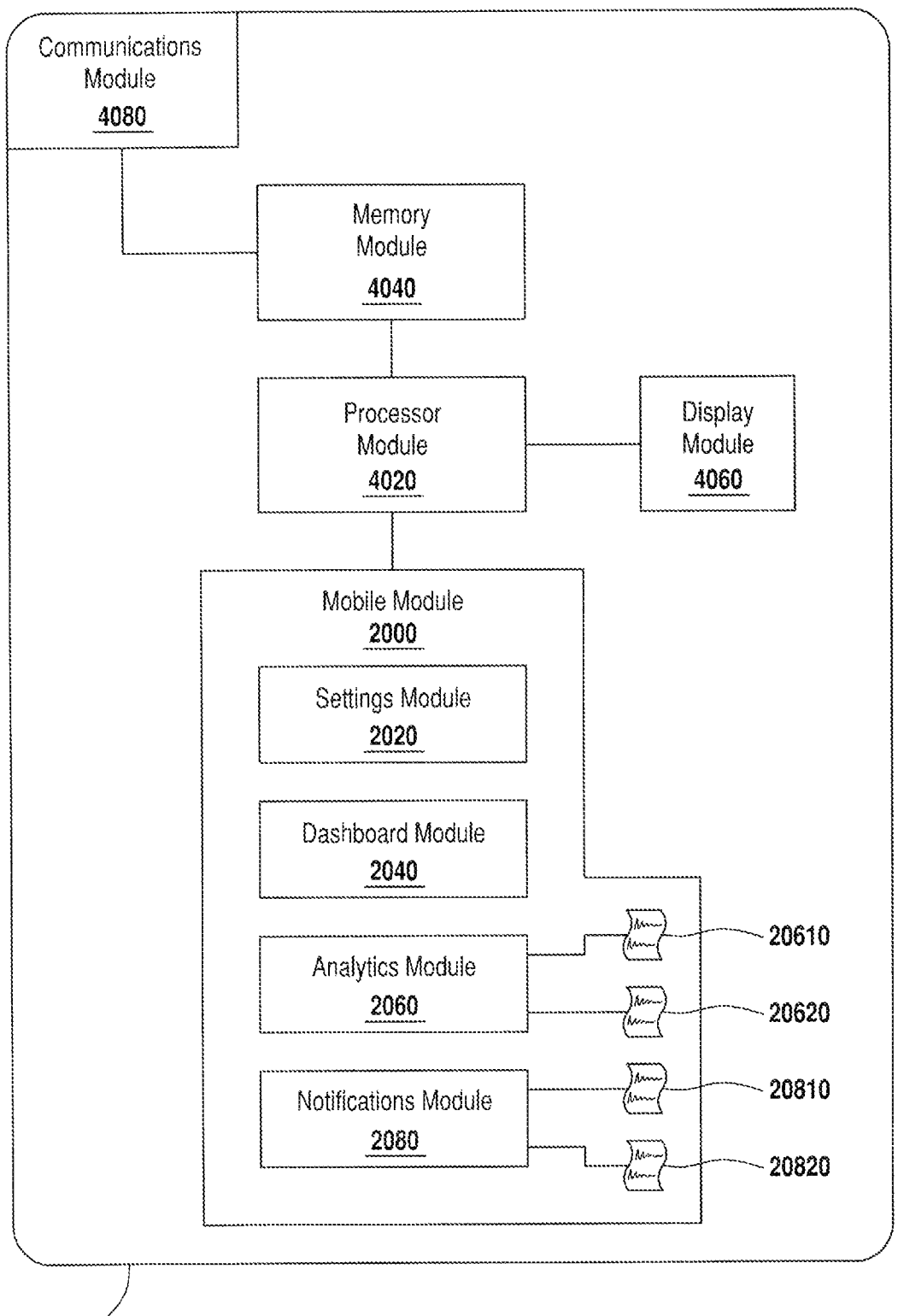
FIG. 6 illustrates a sample schematic of a mobile device at which the mobile module can be implemented.
Figures 9A, 9B:
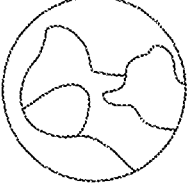
Figure 9G:
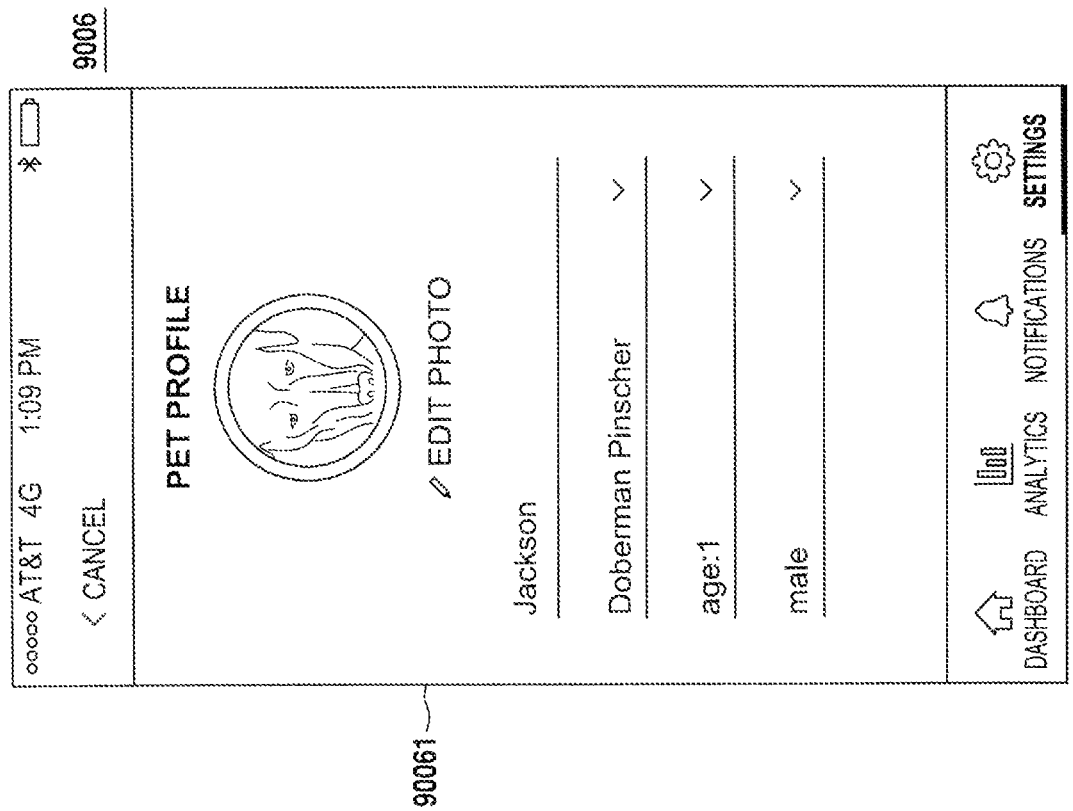

FIG. 6 illustrates a sample schematic of mobile device 4000. Mobile device 4000 comprises processor module 4020 and memory module 4040 coupled together to run mobile device 4000. Memory module 4040 can comprise an operating system which can be accessed therefrom for execution by processor module 4020 to operate different functions of mobile device 4000. In some examples, the operating system can comprise an operating system like an iOS® OS from Apple Computer Inc., an Android® OS from Google, Inc., and/or a Windows Phone OS, from Microsoft, Inc., among others. Mobile device 4000 also comprises display module 4060 coupled to processor module 4020 and configured to present one or more user interfaces for the operation of mobile device 4000. Processor module 4020 is also coupled to communications module 4080, which can be configured to establish connection 6100 (FIG. 3) via one or more of the wireless standards described above.

Mobile module 2000 is also shown in FIG. 6 as implemented in mobile device 4000, and can be coupled to or accessed by processor module 4020 and/or display module 4060. Although shown separate from memory module 4040 in FIG. 6, mobile module 2000 can be coupled to and/or stored at memory module 4040 in some embodiments. For instance, mobile module 2000 can comprise a mobile application (mobile app) which may be downloaded via Internet 6000 from a website or an online application store, and/or which may be stored at mobile device 4000.

As shown in FIG. 3, mobile module 2000 can be configured to provide user 3000 with access to animal sensing/monitoring devices 60 in the animal environment 20 via Internet 6000 through connection 6100 between mobile device 4000 and Internet 6000 and through connection 6200 between Internet 6000 and animal environment 20. Mobile module 2000 can thus allow user 3000 to engage in remote monitoring of the animal 40. Such monitoring can comprise, for example, the review of animal activity and behavior, including food/water consumption, periods of resting and/or activity, and elimination schedules and routines, among others.

As seen in FIG. 6, mobile module 2000 can comprise several sub-modules, such as settings module 2020, dashboard module 2040, analytics module 2060, and notifications module 2080. An optional login module (not shown) may also be included. If present, the login module can be configured to receive authentication information from a user, like user 3000 (FIG. 3) or an animal health professional, to confirm the user's identity prior to providing access to the sub-modules. As is conventional, the authentication information can comprise a username and/or a password or personal identification number (PIN) in some examples.

Settings module 2020 comprises the various user accounts or profiles, animal profiles, mobile device profiles, and help/support functions. The user has the ability to create and edit these profiles to include their personal and animal information. FIG. 7 illustrates an exemplary embodiment of a display 9002 comprising user settings including name 90021, communication information (e.g., e-mail) 90022, and a photo 90023 of the user. FIG. 8 illustrates and exemplary embodiment of a display 9004 comprising user settings including one or more animal profiles 90041 being monitored by device(s) 60. These profiles 90041 are created by providing various details 90061 about the animal, as illustrated in displays 9006a-9006g of FIGS. 9A-9G.

Figures 10, 11:
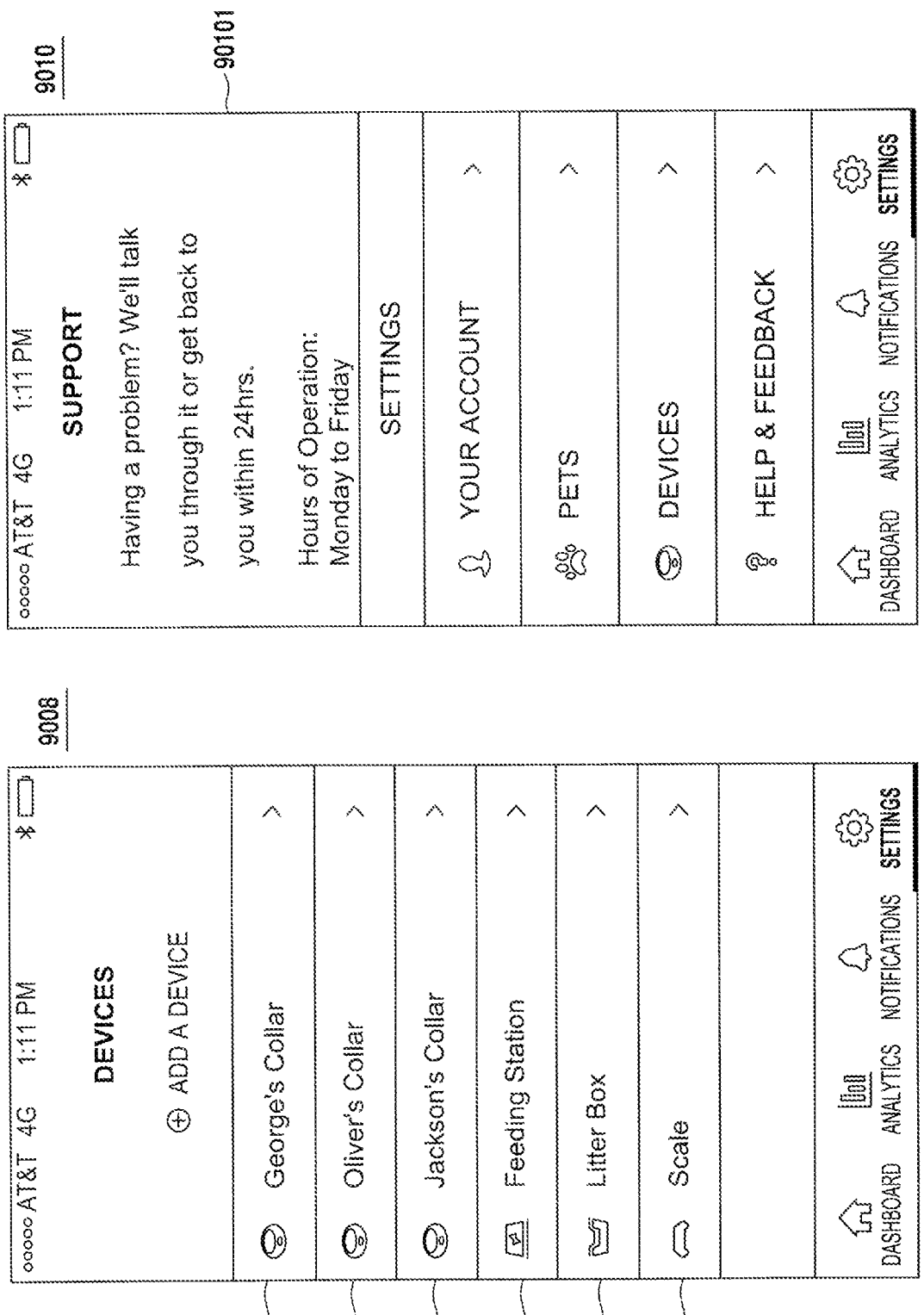
FIG. 10 illustrates an exemplary device profile display of the mobile module.
FIG. 11 illustrates an exemplary help/support display of the mobile module.

Also in settings module 2020 is the ability to add device profiles for the various sensing/measuring devices 60, as shown in exemplary display 9008 (FIG. 10). This may include, for example, collar 90081, feeding station 90082, litter box 90083, and/or scale 90084 embodiments such as those discussed above. The settings module may also include help and/or support functionality 90101, as shown in display 9010 (FIG. 11).

Figure 12C:
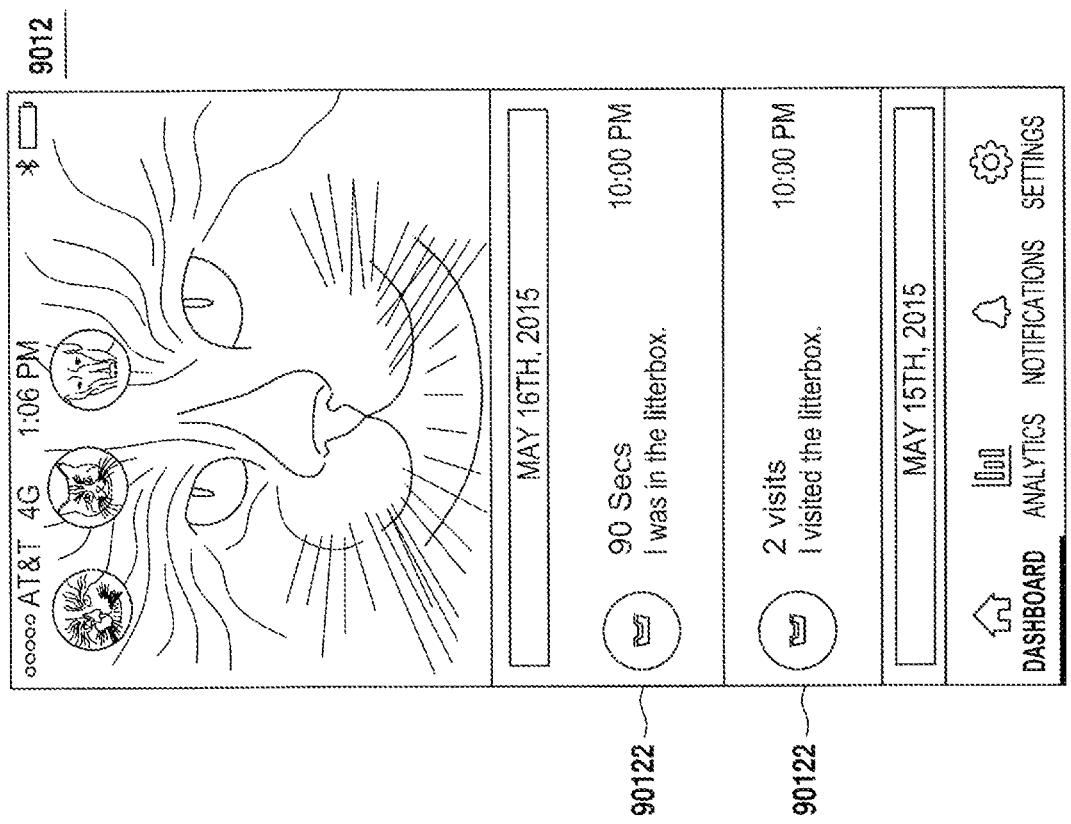
Figures 13A, 13B:
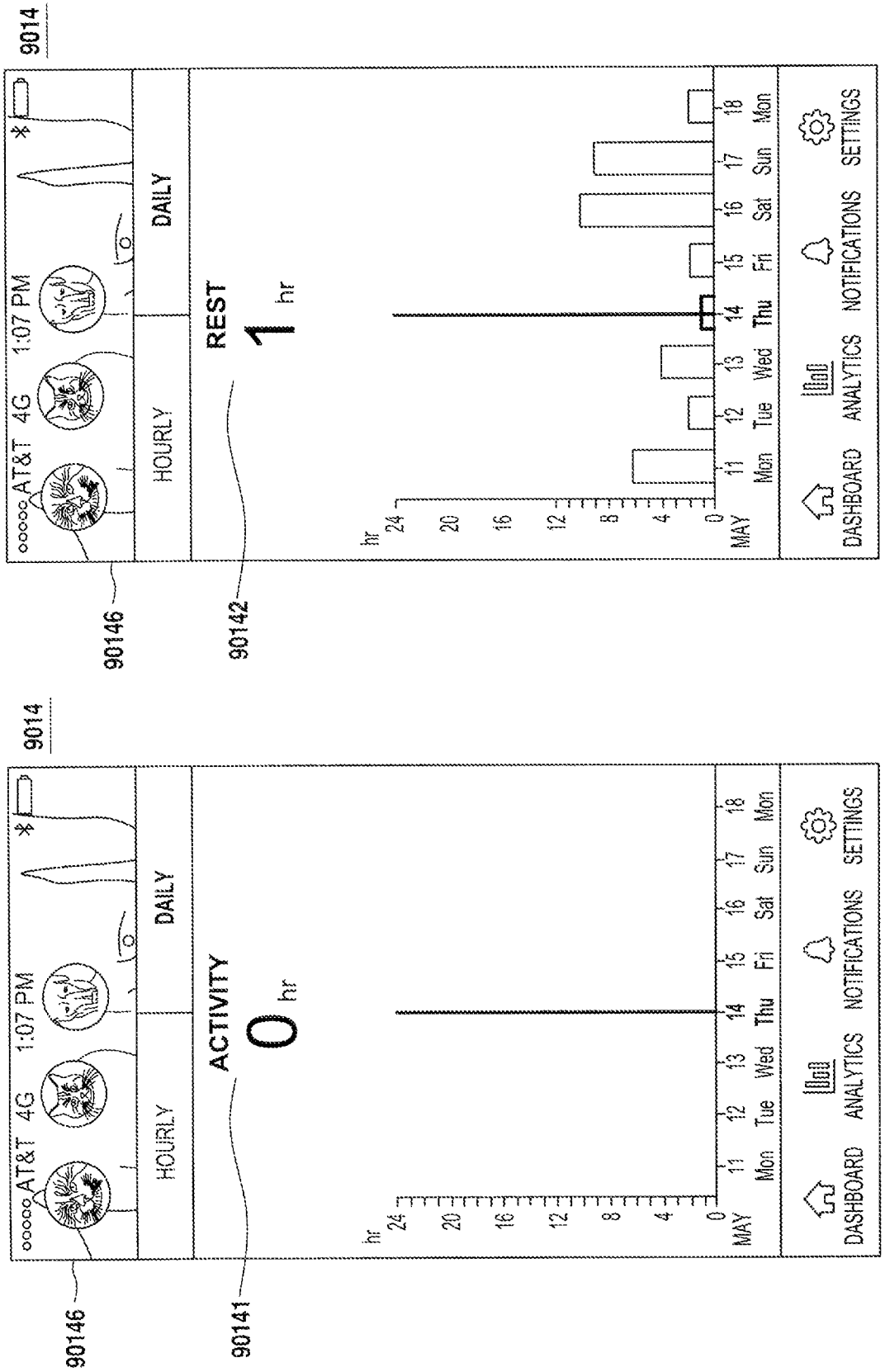
Figure 13E:
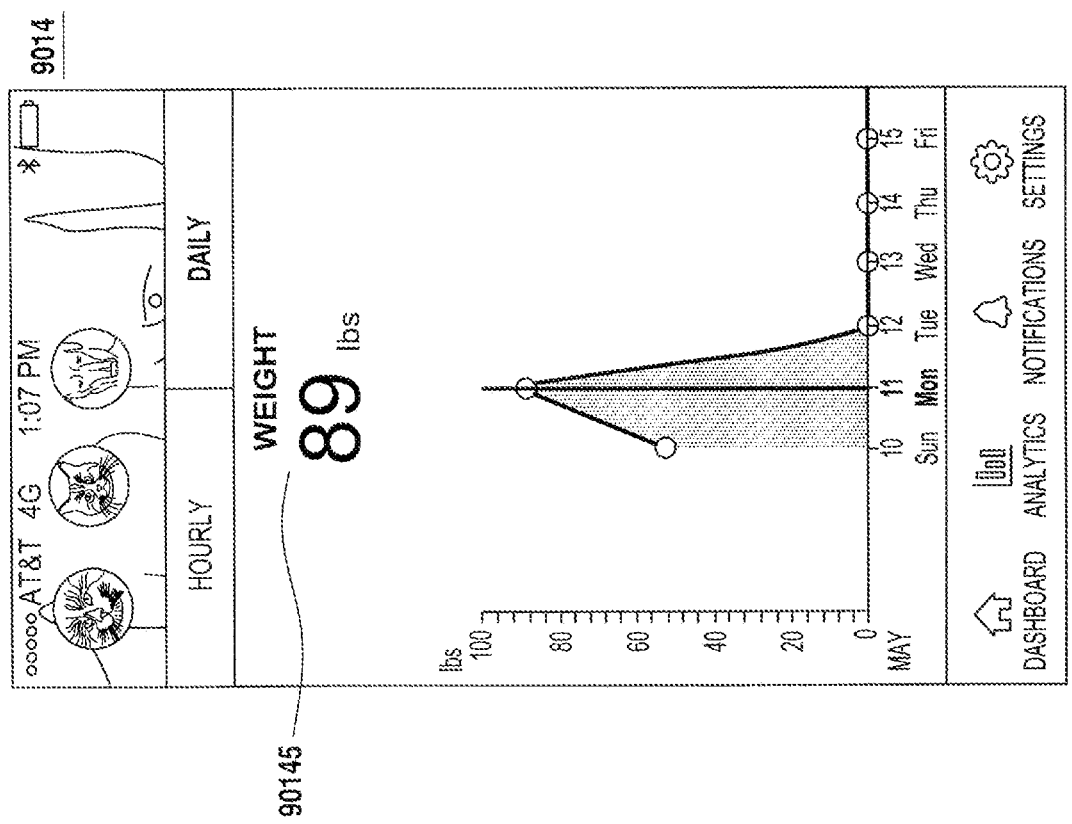
Figure 15:
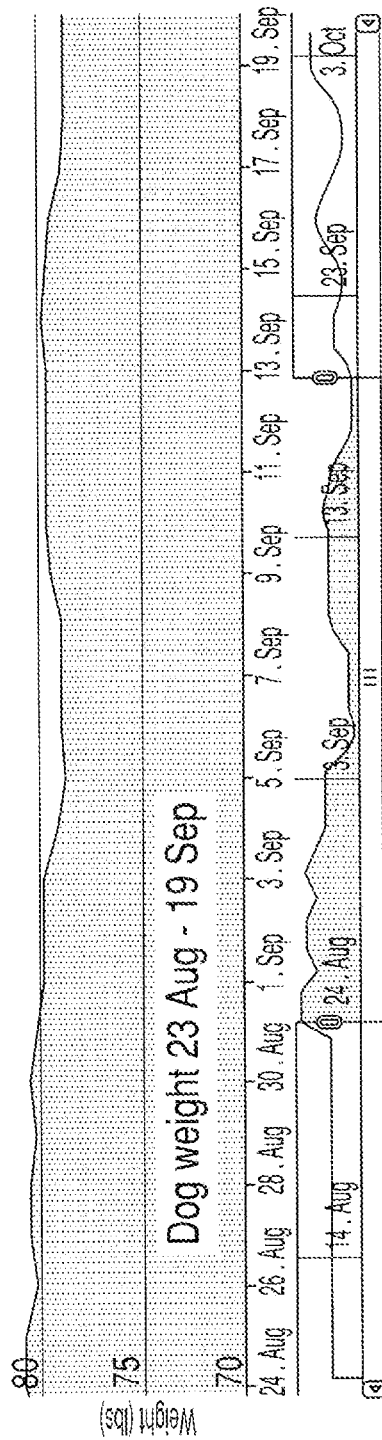
Figure 16:
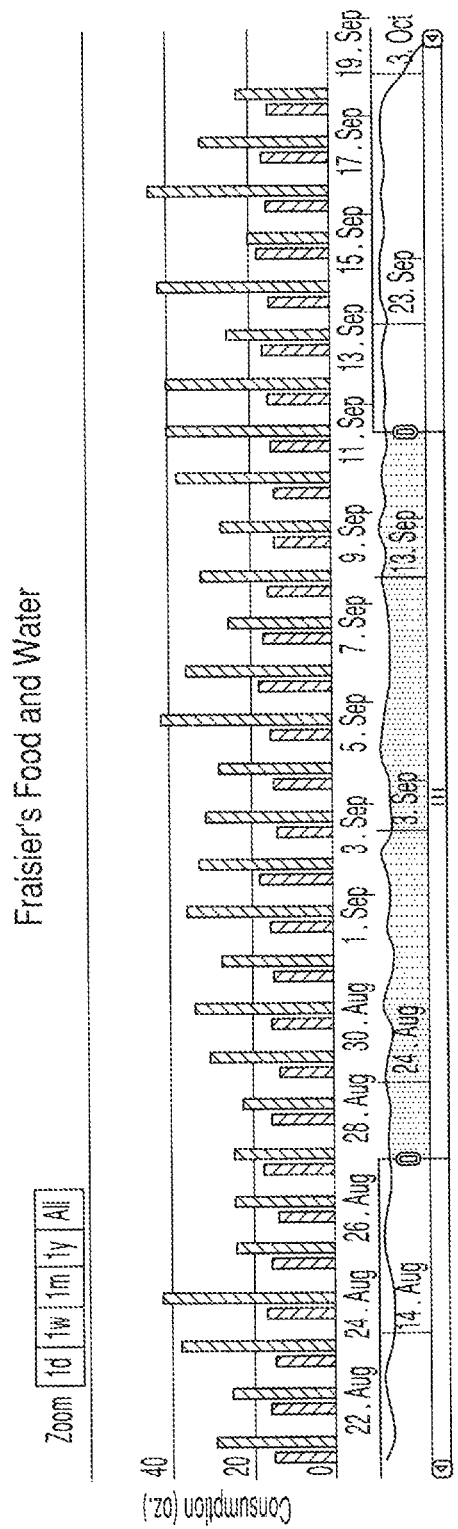

Turning now to the dashboard module 2040, this module comprises analytics-generated messages (e.g., pet health and wellness information) and system information messages (e.g., device power, connectivity, etc.). FIGS. 12A-12C illustrate exemplary embodiments of displays 9012a-9012c. Here, activity information regarding the animal, as detected by the various devices 60, are conveyed to the user via the mobile device 4000. As shown, the activity information may include eating/drinking activity 90121, litter box/elimination activity 90122, and/or physical activity/resting details 90123.

Next, the analytics module 2060 comprises individual data stream details by data type and animal, as collected by device(s) 60. FIGS. 13A-13E illustrate exemplary embodiments of displays 9014a-9014e showing such data stream details as activity 90141, rest 90142, food consumption 90143, water consumption 90144, and weight 90145 for a selected animal 90146. These details may be provided and displayed in variety of ways, including, for example, the depicted graphs charting day, time, amount, etc., or by way of other charts/graphs and/or illustrations. The user can have the ability to tailor the displays to his or her liking, e.g., via the settings module. The analytics module may also be configured to generate and present reports 20610, 20620 including the data stream details, which can, in turn, be printed, saved, and/or shared as part of an animal "journal" or "log" discussed below.

Turning now to the notifications module 2080, this module comprises additional analytics and system information messages. For example, FIG. 14A illustrates and exemplary embodiment of a display 9016a showing details 90161 regarding if/when a selected animal 90162 has interacted with one or more of the sensing/measurement devices 60. Notifications module 2080 may also include "journal"- or "log"-type functionality, in which captured behaviors or activities (such as eating or drinking, as illustrated in exemplary display 9016b (FIG. 14B) are logged or recorded in the module. Here, such relevant or potentially relevant information, including user tagged messages 90163, can be collected and saved for sharing, e.g., with the veterinarian or health care provider of the selected animal 90162. In addition, and similar to the analytics module 2060, the notifications module may also be configured to generate and present reports 20810, 20820 including analytics and system information details, which, in turn, can be printed, saved, and/or shared as part of the animal's "journal" or "log."

In some instances, the exemplary modules described above may be implemented as machine-accessible instructions utilizing any of many different programming codes stored on any combination of machine-accessible media embodied in a mobile application (e.g., an app) and/or an online application for various wired and/or wireless mobile communication devices such as handheld computers, smartphones, portable media players, tablet computers, etc. In addition or alternatively, the machine-accessible instructions may be embodied in a volatile or non-volatile memory or other mass storage device (e.g., a USB drive, a CD, or a DVD). For example, the machine-accessible instructions may be embodied in a machine-accessible medium such as a programmable gate array, an application specific integrated circuit (ASIC), an erasable programmable read only memory (EPROM), a read only memory (ROM), a random access memory (RAM), a flash memory, a magnetic media, an optical media, and/or any other suitable type of medium. The systems, apparatus, methods, and articles of manufacture described herein are not limited in this regard.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

All elements claimed in any particular claim are essential to the embodiment claimed in that particular claim. Consequently, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are expressly stated in such claims.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

Having described the invention in detail, it will be apparent that modifications and variations are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Unexpected Dog Weight Loss Identification

This example describes how multiple types of data acquired on a single pet, longitudinally, were be leveraged to identify significant and/or unexpected changes in pet health and wellness based on the assessment of each data types trends over time when compared to one another.

Methods

Several devices were used in a typical animal-owning home environment to acquire specific data about a standard poodle named Frasier. Each device leveraged technologies to acquire and transmit data from the animal across a home wireless network to the "cloud" where it was stored and analyzed. Once analyzed, the data was then made available to the animal owner to view through a secure web-site (User Interface, "UI") on a computer or smart device with internet access. The devices utilized rechargeable batteries and/or connectivity to standard household electrical outlets to ensure data was acquired on the animal continuously over an extended period of time.

The type of data acquired determined how that data was presented in the UI. For example, dog weight in the UI represents the average of all daily weights acquired by the scale each day. Food and water consumption shown in the UI represents the total net weight (in ounces) of each consumed in a day. Activity levels were defined as distance travelled in a day based on accelerometer data acquired through a dog collar device.

Materials

In this case, three separate devices were used to acquire specific data about Frasier; 1) a collar-mounted device including an accelerometer used to track activity levels, 2) a device that tracks food and water consumption from Frasier's food and water bowls using standard load cells and 3) a 2'×3' scale device that tracks Frasier's weight using load cells.

While it is normal for animals to receive food and water outside of their food and water bowls, it was assumed that most animal owners tend to be relatively consistent in their feeding and hydration patterns for animals outside of their normal food and water bowls, which makes that behavior constant over time. Also, in this case, the scale used was placed in front of the food and water bowls, which ensured Frasier's weight was recorded each time he ate/drank from the these bowls. Frasier's weight could also be captured by placing the scale anywhere in the home where he would be motionless for some period of time on a regular bases (such as under a dog bed, dog crate, etc.).

Once each of the devices was positioned in the home and connected to the home wireless network, Frasier's profile was created in the UI and power was maintained with each of the devices, whereby the data that was acquired from each device flowed through the technical architecture to the UI where the data could be viewed by the pet owner at any time. Views of the data could be manipulated through the UI to enable data views across multiple time horizons (daily, weekly, monthly, yearly, all data, etc.).

Results

When observing Frasier's data over a 4 week period (FIGS. 15-18), it was clear that 3 of the 4 data stream trends being tracked remained relatively stable during this period. It was also observed that his weight reduced significantly during this period (from a high of 80.3 lbs to a low of 78.8 lbs (FIG. 18)). This represented a 1.9% decrease in total body weight during this period which can be significant especially given the consistent negative trend in weight that was observed during this time period. To put this in perspective, this rate of decrease extrapolated over a single year would represent almost a loss of nearly one-fourth the total body weight which, intuitively, represents an unhealthy weight loss.

It could be possible for this level of weight loss to be attributed to other factors such as increased activity levels and/or changes in food and water consumption levels. In this case, the ability to observe other types of data on Frasier during the same time further highlights the potential for concern over his weight loss. In this case, it was observed that food and water consumption trends remain relatively constant, as does Frasier's level of activity (all within normal ranges of variability). As a result of these other data types, one would not expect to see such a significant decrease in total body weight during this period.

This example highlights how the ability to acquire and view a animal's data over an extended period of time can identify insights into potential health and wellness concerns that might not be obvious to the pet owner. If Frasier's weight had been the only data tracked, it could have been possible to overlook the significance of the weight change by not seeing actual food/water consumption and activity data. The ability to see multiple, relevant data types on a single animal, longitudinally, provided surprising insight into our ability to analyze and assess changes in the data that might indicate changes in relative trends that can identify the potential of increased levels of risk to the pets health and wellness.

In Frasier's case, a trip to the veterinarian at the end of this test period resulted in a series of tests that concluded that Frasier was in a relatively advanced stage of cancer of the lymph nodes. While this data led to a diagnosis that afforded him the opportunity to receive treatment for his cancer, he lived only about 7 months following this diagnosis. Had this data been tracked on Frasier much earlier, relative changes in the data could have been identified earlier that would have led to an earlier cancer diagnosis and, subsequently, a better outcome; more time and/or options for treatment and/or increased opportunity for a resolution to the disease or to extending his lifespan.

Examples 2A and 2B—Cat Elimination Behavior Tracking

The following two examples detail how data acquisition leveraging sensor technologies can be used with cats to gain early insights into changes in elimination behavior patterns, that aren't visible to cat owners, but which can enable insights into increased risks associated with the early onset symptoms of common diseases that impact the length and quality of life of cats such as diabetes, leukemia, kidney disease, etc. While the types of data acquired in each of the following cases is identical, the methods of data acquisition were different, illustrating how different sensing technologies can be used to capture relevant data.

Example 2A—Weight Sensing

Methods

This example describes a case where a prototype weight-sensing device was placed under a cat litter box in a typical cat-owning home environment to acquire specific data about a cat. The device used motion/movement detection technology to acquire data from the cat's engagement of the litter box and stored that data on the device, which was subsequently connected to a laptop/pc for data export and analysis using a standard data analysis tool. FIGS. 19-23 are illustrations of the data acquired for a single cat using a single litter box in a typical home environment.

The type of data acquired in this case was the presence (or absence) of weight in a litter box beyond the normal weight of the box plus the litter in the box. The presence of additional weight indicated cat activity in the litter box. When the cat was not present in the litter box, no change in weight was detected. However, as soon as the cat put weight on/in the litter box an engagement event was initiated. The end of an event is identified by time-stamp once the weight of the cat is no longer measured by the device. Knowing the start/stop time of each event enables the calculation of event frequency, event duration and litter box use-patterns in the case of multiple litter boxes existing in a single home (in this case, only one litter box was used for data collection purposes but extending the analysis of data to include multiple litter boxes and even multiple cats is an intuitive extension of this case that can be realized leveraging the same technologies as described in this case).

Materials

For simplicity, in this case only one device was used to acquire specific data about a single house cat in a normal home environment. The device consisted of a metal platform upon which the litter box was placed. On one end, the platform was slightly elevated by an adjustable spring that enabled one end of the platform with litter box and litter to be raised or lowered slightly. Underneath the platform was a small base that included a "contact" post attached to a standard USB data-writer. When properly adjusted the platform was elevated ⅛" to ½" above the contact post with only the litter-filled litter box on the platform. When properly adjusted, the cat entering the litter box compressed the spring due to the cats weight being added to the system making contact with contact post. This contact closed a circuit that triggered a data point and date/time stamp to be written to the data-writer device signifying the start of an event. As the cat moved in the litter box, a properly tensioned spring would cause the contact between the platform and contact post to be broken and re-established, writing a series of data points over time to the data-writer that confirm event activity is continuing in the litter box.

When the cat left the litter box, the spring tension broken the connection between the platform and connection post which then stayed broken indicating the end of the litter box engagement event.

This test can be easily extended, utilizing the same device and technologies, to include multiple litter boxes and multiple cats in a single home. This would expand the data analysis to include tracking the individual litter box engagement patterns of each cat as a measure of normal behaviors and changes to normal behaviors which can be significant. In the case of multiple cats in a home, the system must be able to discern which cat is responsible for each litter box engagement event, which can be accomplished in a variety of ways including RFID or Bluetooth Low Energy (BLE) tags on the cat collar or through development of algorithms capable of identifying cats uniquely based on "signature" patterns in the data acquired.

At any point in time, the data files in the data-writer could be connected to a laptop/pc via USB connection and the files imported into MS Excel or other data analysis tools to manually track event frequency, duration and time of day patterns and their changes over time.

Results

The data described FIGS. 19-23 was collected on a single cat using a single litter box over multiple days. While no software-based algorithms or analytics were designed into the prototype system that acquired this data, observation and manual analysis of the data clearly illustrate the ability to identify litter box engagement patterns such as event frequency, duration and time-of-day patterns and the level of variability that exists within and across these measures.

Figure 19:
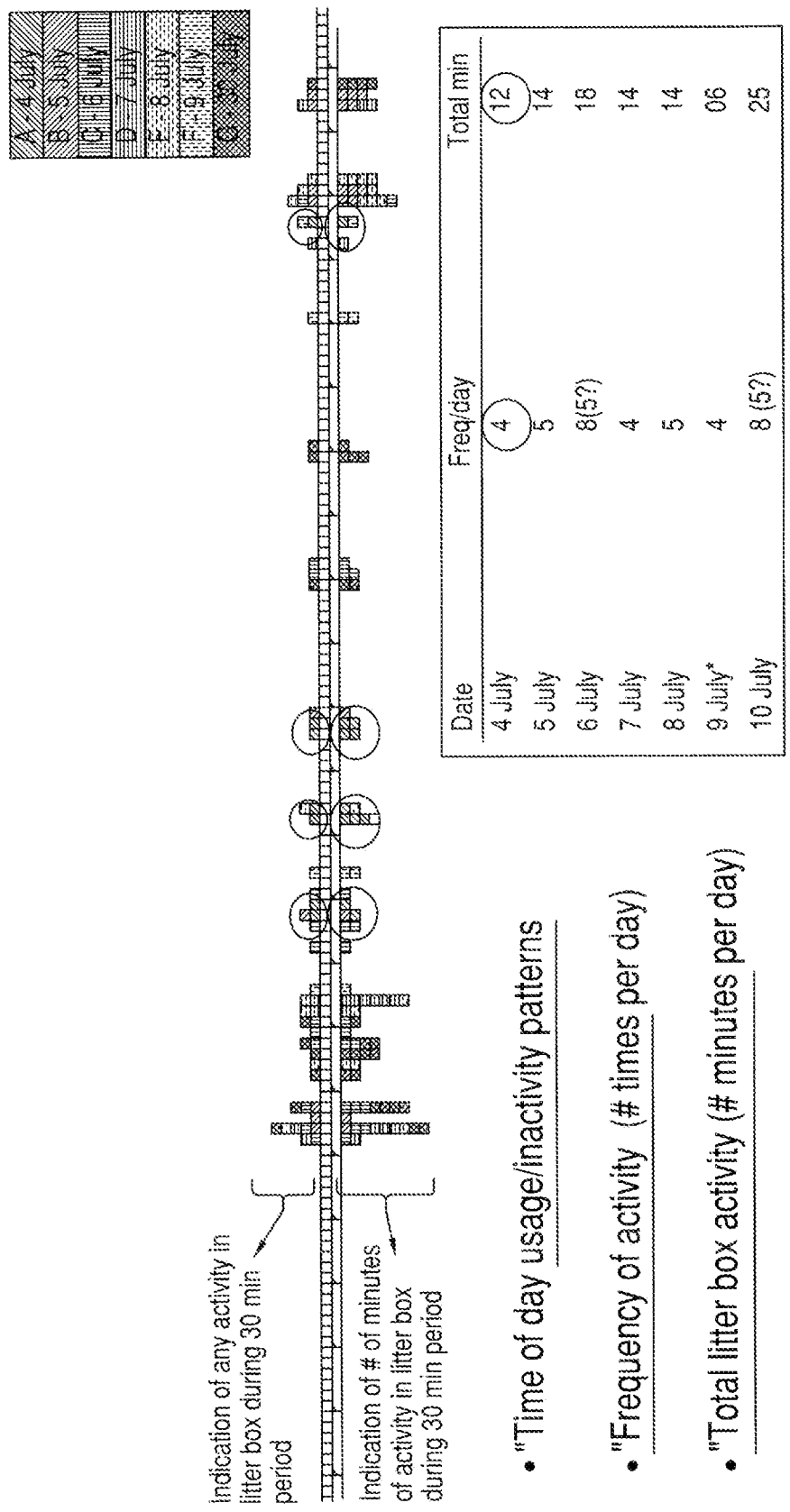
Figure 20:
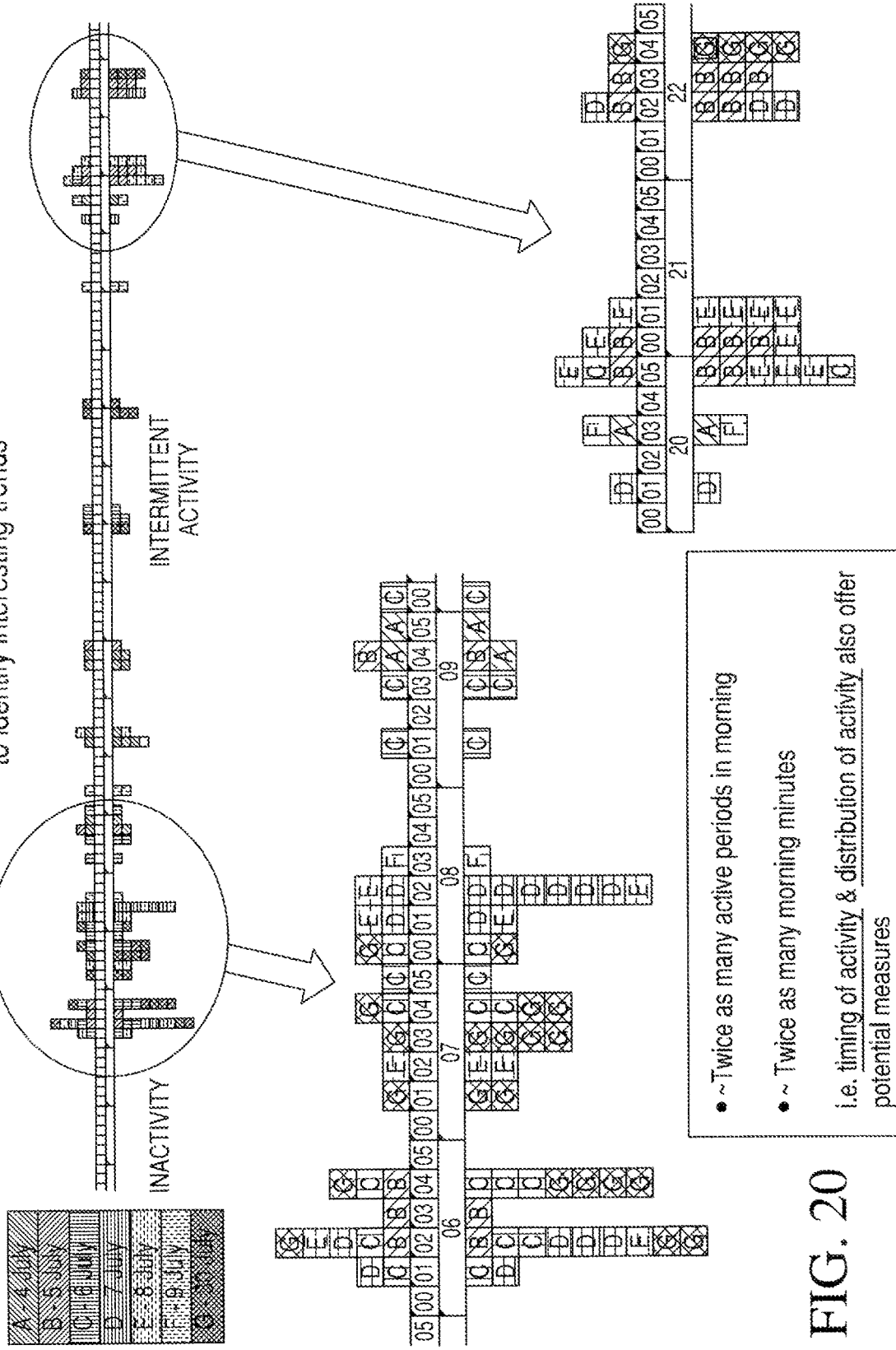
Figure 21:
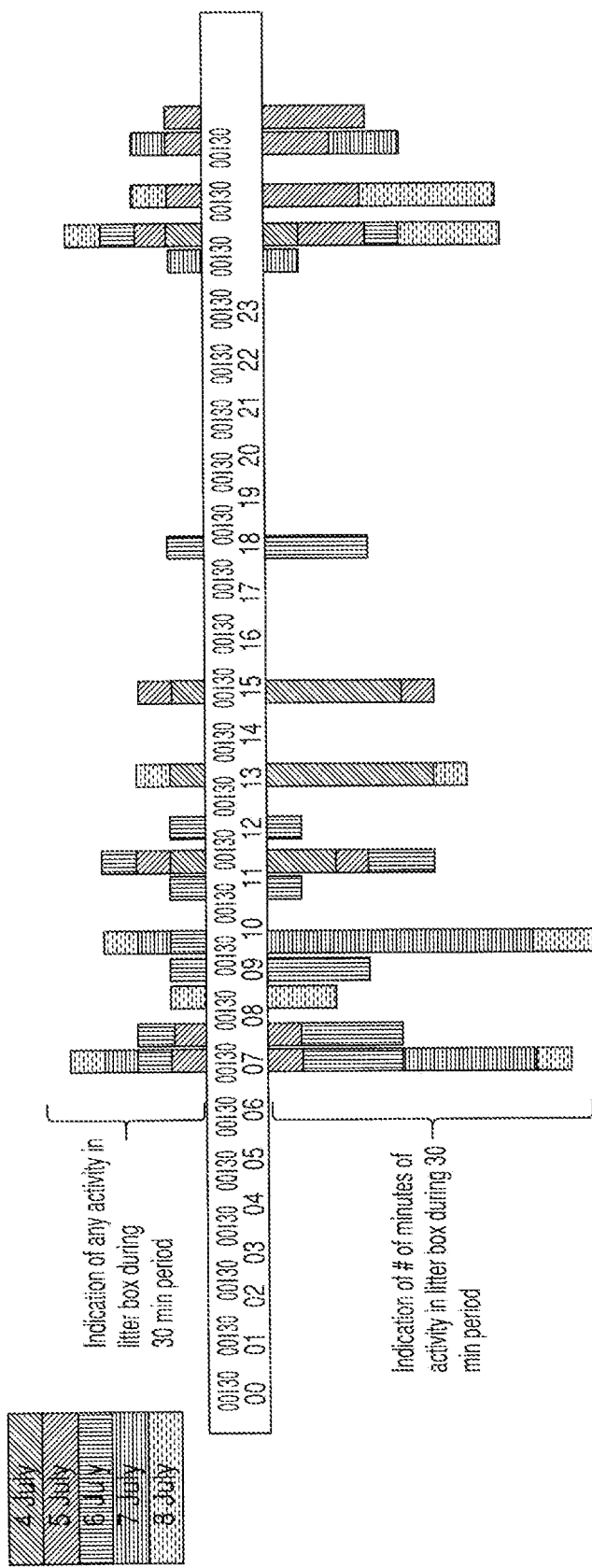

The data in FIG. 19 describes activity in the litter box over seven days. When each litter box engagement day's data is plotted on a 24 hour time scale, normal use patterns of both frequency and duration become evident, as well as, variability in patterns which could signify negative trends in health including the possibility of early disease symptom onset. Among the interesting features of this data set is how it can be used to illustrate changes in cat elimination behavior patterns as a result of non-normal external stimuli on the cat. For example, on July 4th, the litter box engagement pattern of the cat seems normal during the day but is unusually low in the evening when compared to other nights. This happened to be an evening when fireworks were being set off at the next house in celebration of the 4th of July holiday, causing the cat to stay hidden. Another example illustrated by this data is seen on July 9th. On this day, the frequency of elimination, while low, falls within the normal range of variability but the total duration of activity for this day was significantly less than any other day during this test period (6 minutes of total activity this day compared to 12-25 minutes of activity every other day). This day was unique for the cat as its home owner hosted a large dinner party for 30-40 guests that afternoon/evening and there was therefore an unusual amount of activity in the home throughout the day in before/during/after that brought many visitors into the home throughout the day who were unfamiliar to the cat. As a result, the cat's litter box engagement pattern was impacted by significantly reducing the amount of time spent in the litter box during each event in order to avoid/hide from the unusual activity in the home that day. The following day (July 10th), the cat spent a significantly greater time in the litter box than normal.

Figure 17:
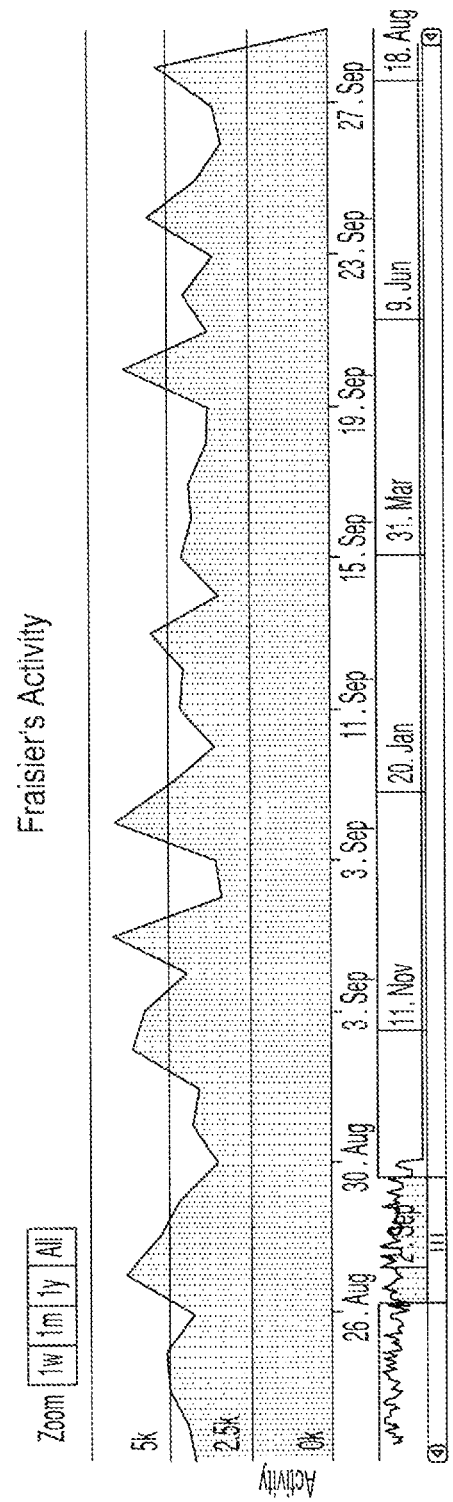

FIGS. 17-18 illustrate the opportunity to leverage this data to identify additional metrics that may be of value in assessing cat elimination behavior patterns and changes to patterns that may be of significance. In this case, the data can be shown to also identify patterns of normal litter box usage in terms of time of day patterns and cumulative duration patterns during certain times of day. In addition to event frequency and duration, it is likely that changes to time of day usage patterns in the litter box can be used to identify periods of stress or changes in health and wellness from the cats normal baseline. In the case of a multiple litter box home, it is also likely that changes in box choice patterns over time can be used to identify significant changes in behavior which may indicate significant changes in cat behavior. In the case of a multiple cat and/or multiple litter box home, it is also likely that changes in cat behavior patterns relative to one another can be compared to gain new insights into individual cat behavior patterns of interest, as well as, to gain understanding into normal interactions between cats in a home and changes to those patterns that may be of importance.

Example 2A—Motion/Movement Sensing

This example describes how data acquisition leveraging sensor technologies can be used with cats to gain early insights into changes in elimination behavior patterns that are not visible to cat owners, but which can enable insights into increased risks associated with the early onset symptoms of common diseases that impact the length and quality of life of cats such as diabetes, leukemia, kidney disease, etc.

Methods

This example describes a case where a motion/movement detection device was placed on a cat litter box in a typical cat-owning home environment to acquire specific data about a cat. The device used motion/movement detection technology to acquire and transmit data from the litter box and across a home wireless network to the "cloud" where it was stored and analyzed. Once analyzed, the data was them made available to the cat owner to view through a secure web-site (User Interface, "UI") on any computer or smart device with internet access. The device used rechargeable batteries and/or connectivity to standard household electrical outlets to ensure data was acquired on this animal continuously over an extended period of time.

The type of data acquired in this case was motion (or lack of motion) in a litter box, which was in turn used as an indicator of cat activity in the litter box. When the cat was not present in the litter box, no motion was detected. However, as soon as the cat touched the litter box the sensor recognizes motion which indicates the start of a litter box engagement event by the cat. During the event, there may be short periods of time when motion is/isn't detected, but the event termination can be clearly seen when motion data ceases to be acquired for an extended period of time. The start and stop of each litter box engagement event is timestamped by the system which enables the calculation of event frequency, event duration and litter box use-patterns in the case of multiple litter boxes existing in a single home (in this case, only one litter box was used for data collection purposes but extending the analysis of data to include multiple litter boxes and even multiple cats is an intuitive extension of this case that can be realized using the same technologies as described in this case).

Materials

For simplicity, in this case only one (1) device was used to acquire specific data about a single house cat in a normal home environment. The device used included a standard accelerometer sensor and other componentry that enabled the ability to acquire, store and transmit relevant data. The components were housed in a plastic case measuring approximately 2" deep×3" height×6" depth and attached to any standard litter box using a heavy duty double stick Velcro® tape. The device was connected to normal household electrical power but was also designed so that it could also be powered by re-chargeable battery.

This test can be easily extended, leveraging the same technologies, to include multiple litter boxes and multiple cats in a single home. This would expand the data analysis to include tracking the individual litter box engagement patterns of each cat as a measure of normal behaviors and changes to normal behaviors which can be significant. In the case of multiple cats in a home, the system must be able to discern which cat is responsible for each litter box engagement event which can be accomplished in a variety of ways such as RFID or Bluetooth Low Energy (BLE) tags on the cat collar or through development of algorithms capable of identifying cats uniquely based on "signature" patterns in the data acquired.

Once the device was set-up in the home and connected to the home wireless network, the cat's profile was created in the UI, power was provided to the device, and the data that was acquired flowed through the technical architecture to the UI where the data could be viewed by the cat owner at any time. Views of the data could be manipulated through the UI to enable data views across multiple time horizons (daily, weekly, monthly, yearly, all data, etc.).

Results

Figure 22:
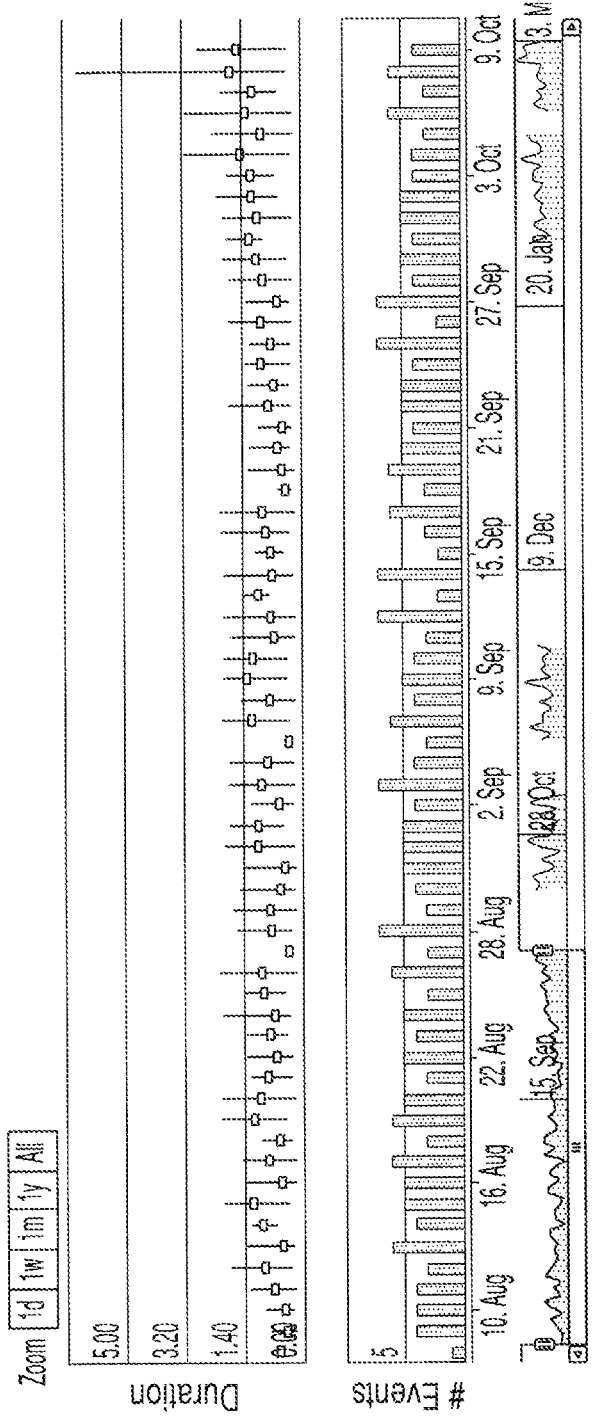
Figure 23:
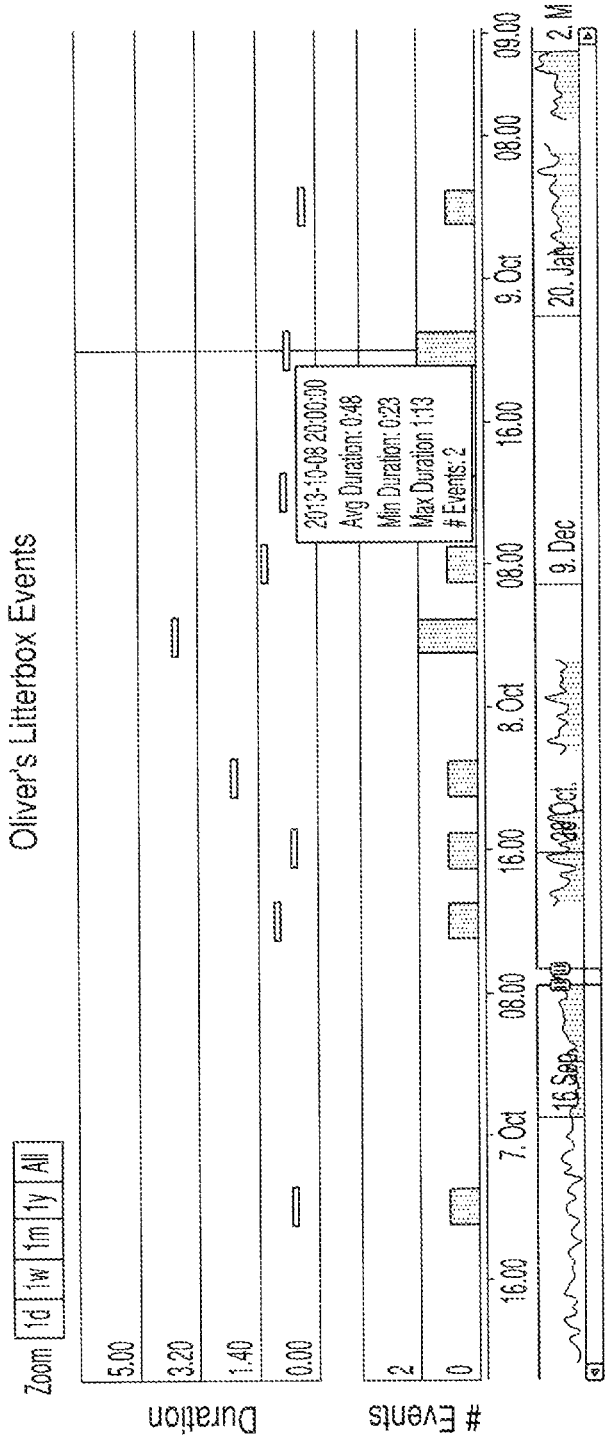

The data was collected on a single cat using a single litter box over a two month period (FIGS. 22 and 23). FIG. 22 illustrates the ability to identify a daily event frequency, as well as to identify the min/max/average time spent in the litter box per event for that day. FIG. 23 illustrates the ability to track each event uniquely during a given day. While no software-based algorithms or analytics were designed into the prototype system that acquired this data, observation and manual analysis of the data clearly illustrate the ability to identify litter box engagement patterns such as event frequency, duration and time-of-day patterns and the level of variability that exists within and across these measures. Leveraging existing technologies, the capability exists to automate the analysis of this data to develop "normal" baseline behavior patterns and identify changes to these patterns that could indicate increased risk of a negative health trend that might indicate the early onset of a medical condition, disease or health-risk. These patterns could be identified using statistical/mathematical models and/or heuristics or common rules accepted or known in veterinary and/or animal wellness practices.

What is claimed is:

1. A method of preparing a nutrition, health, and/or wellness recommendation for an animal, the method comprising:
    collecting data on a plurality of parameters, wherein each of the plurality of parameters is selected from the group consisting of health, diet, behavior, and environmental parameters of the animal, wherein the data is collected on an automated basis continuously or at periodic intervals, and the data is collected by (a) a worn sensor that is coupled to at least one of a collar or a leash worn by the animal and (b) a location sensor that is a stationary sensor located at a location frequented by the animal,
    wherein the location sensor comprises a weight monitor placed under a kennel or a sleeping or resting location of the animal, the weight monitor provides real-time weight tracking;
    wherein at least one of the stationary and location sensors comprises a component selected from the group consisting of accelerometers, gyroscopes, weighing scales, weight transducers, force transducers, displacement transducers, orientation sensors, pressure transducers, weight sensors, force sensors, pedometers, displacement sensors, pressure sensors, load cells, photographic cameras, video cameras, camcorders, RF location beacons, contact thermometers, non-contact thermometers, laser thermometers, infrared pyrometers, laser pyrometers, optical sensors, optical reflecting sensors, LED/photodiode pair optical sensors, LED/phototransistor pair optical sensors, laser diode/photodiode pair optical sensors, laser diode/phototransistor pair optical sensors, optocouplers, optical fiber coupled optical sensors, magnetic sensors, inductive proximity sensors, magnetic proximity sensors, capacitive proximity sensors, global positioning system devices, global navigation satellite system devices, and a combination thereof;
    storing the data in a cloud-based architecture;
    analyzing the data, wherein the analyzing is performed automatically by a processor and comprises the processor applying a filter for tracking a mean of each of the plurality of parameters of the animal and an atypical derivation from a baseline of each of the plurality of parameters of the animal, wherein the analyzing further comprises the processor determining whether the atypical derivation is a random event or is a trend;
    producing, on the processor, an outcome from the analyzing of the data;
    calculating, on the processor, a level of the outcome;
    determining, on the processor, whether the level of the outcome is above or below a threshold, wherein the determining prompts generation of the nutrition, health, and/or wellness recommendation for the animal, wherein the nutrition, health, and/or wellness recommendation recommends a nutritional or feeding change for an individual to perform to improve well-being of the animal; and
    providing, by the processor, the nutrition, health, and/or wellness recommendation based upon the analyzed data.

2. The method of claim 1 wherein the nutrition, health, and/or wellness recommendation recommends that the individual perform one or more changes in environment for the animal.

3. The method of claim 1 wherein the plurality of parameters comprises a health parameter of the animal selected from the group consisting of the animal's age; sex; gender; species or breed; body weight; body mass index (BMI); body composition; body temperature; gait force; reproductive aspects; skin and coat condition; cardiovascular system; gastrointestinal and kidney functions; vision health; cognitive health; and combinations thereof.

4. The method of claim 1 wherein the plurality of parameters comprises a diet parameter of the animal selected from the group consisting of (i) the animal's food and water consumption and amount and time of day thereof; (ii) nutritional profile of the food consumed; (iii) vitamin, supplement, and/or medication consumption; and (iv) combinations thereof.

5. The method of claim 1 wherein the plurality of parameters comprises a behavior parameter of the animal selected from the group consisting of (i) an activity profile comprising one or more of calories burned, steps or distance traveled, intensity levels, changes in elevation, and time of day information; (ii) elimination activity comprising one or more of frequency, amount, and time of day of elimination; (iii) vocalization; and (iv) combinations thereof.

6. The method of claim 1 wherein the plurality of parameters comprises an environmental parameter of the animal selected from the group consisting of (i) weather information comprising one or more of air temperature, humidity, heat index, and precipitation; (ii) location coordinates of the animal; (iii) location coordinates of one or more of food, water, a waste container, sleeping by the animal or resting of the animal; (iv) presence or absence of an owner or caretaker at the location of the animal; (v) presence or absence of a child or elderly individual at the location of the animal; and (vi) combinations thereof.

7. The method of claim 1, wherein the nutrition, health, and/or wellness recommendation additionally recommends that the individual perform administration or cessation of vitamins, supplements, or medication for the animal.

8. The method of claim 1, wherein the nutrition, health, and/or wellness recommendation additionally recommends that the individual perform a veterinary visit for the animal.

9. The method of claim 1, wherein the individual for whom performance of the nutritional or feeding change is recommended by the recommendation is selected from the group consisting of an owner of the animal, a caretaker of the animal, a veterinary for the animal, and combinations thereof.

10. The method of claim 1, wherein a mobile device receives the data and performs the analyzing of the data, and the method further comprises:
- receiving and storing information of a user on a setting module of the mobile device;
- providing analytics-generated messages and system information messages to the user from a dashboard module of the mobile device;
- providing data stream details to the user based upon data type and the animal from an analytics module of the mobile device; and
- providing additional analytics and system information messages to the user from a notifications module of the mobile device.

* * * * *